United States Patent
Kadam et al.

(10) Patent No.: US 9,518,048 B2
(45) Date of Patent: Dec. 13, 2016

(54) PROCESS FOR THE PREPARATION OF TENELIGLIPTIN

(71) Applicant: GLENMARK PHARMACEUTICALS LIMITED; GLENMARK GENERICS LIMITED, Mumbai (IN)

(72) Inventors: Suresh Mahadev Kadam, Thane (IN); Bipin Parsottam Kansagra, Ahmedabad (IN); Ramchandran Vishnue Kale, Rashin (IN); Jayant Prakashrao Patil, Nasik (IN); Venkataramana Reddy Yemireddy, Navi Mumbai (IN); Shailendra Nilkanth Bhadane, Jalgaon (IN); Uddhav Popat Chaudhar, Pathardi (IN); Ulhas Digambar Patil, Kalyan (IN); Shekhar Bhaskar Bhirud, Mumbai (IN)

(73) Assignee: Glenmark Pharmaceuticals Limited, Mumbai (IN)

( * ) Notice: Subject to any disclaimer, the term of this patent is extended or adjusted under 35 U.S.C. 154(b) by 0 days.

(21) Appl. No.: 14/423,550

(22) PCT Filed: Aug. 28, 2013

(86) PCT No.: PCT/IN2013/000527
§ 371 (c)(1),
(2) Date: Feb. 24, 2015

(87) PCT Pub. No.: WO2014/041560
PCT Pub. Date: Mar. 20, 2014

(65) Prior Publication Data
US 2015/0203484 A1    Jul. 23, 2015

(30) Foreign Application Priority Data

Aug. 31, 2012  (IN) .......................... 2544/MUM/2012
Mar. 6, 2013   (IN) ...........................  678/MUM/2013

(51) Int. Cl.
| | | |
|---|---|---|
| *C07D 417/06* | (2006.01) |
| *C07D 231/40* | (2006.01) |
| *C07D 295/205* | (2006.01) |
| *C07D 417/14* | (2006.01) |

(52) U.S. Cl.
CPC .......... *C07D 417/14* (2013.01); *C07D 231/40* (2013.01); *C07D 295/205* (2013.01); *C07D 417/06* (2013.01)

(58) Field of Classification Search
CPC . C07D 417/06; C07D 231/40; C07D 295/205; C07D 417/14
See application file for complete search history.

(56) References Cited

U.S. PATENT DOCUMENTS

| | | | |
|---|---|---|---|
| 7,060,722 B2 * | 6/2006 | Kitajima | C07D 207/16 514/365 |
| 7,074,794 B2 | 7/2006 | Kitajima et al. | |
| 2004/0106655 A1 | 6/2004 | Kitajima et al. | |

FOREIGN PATENT DOCUMENTS

| | | | |
|---|---|---|---|
| EP | 1854795 A1 | 11/2007 |
| EP | 1894567 A1 | 3/2008 |

* cited by examiner

*Primary Examiner* — Sun Jae Yoo
(74) *Attorney, Agent, or Firm* — M. Carmen & Associates

(57) ABSTRACT

A process for the preparation of teneligliptin.

10 Claims, 5 Drawing Sheets

Glenmark Generics limited

PROCESS FOR THE PREPARATION OF TENELIGLIPTIN

PRIORITY

Figure 1:
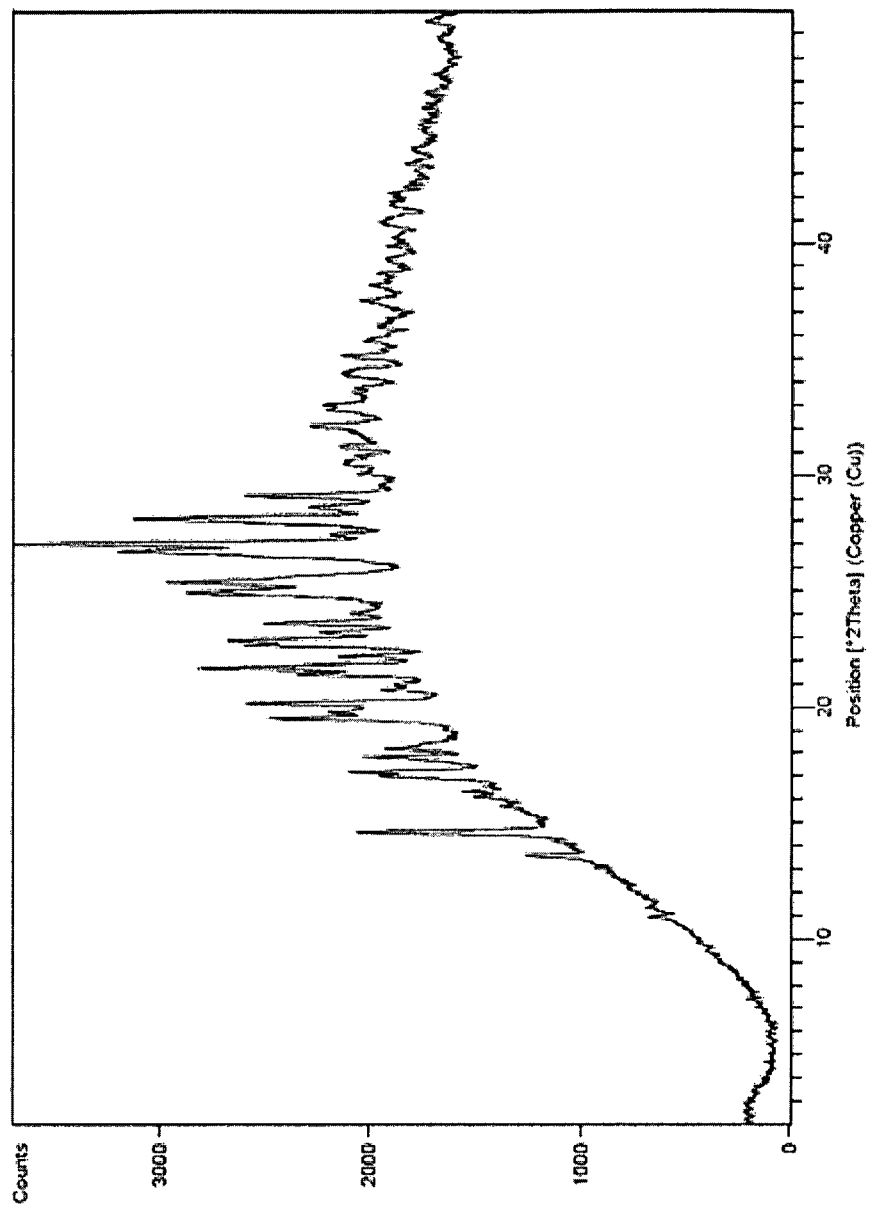

This application claims priority under 35 U.S.C. §371 to International Application No. PCT/IN2013/000527, filed Aug. 28, 2013 which claims the benefit under 35 U.S.C. §119 to Indian Provisional Application No. 2544/MUM/2012, filed on Aug. 31, 2012 and Indian Provisional Application No. 678/MUM/2013 filed on Mar. 6, 2013, the contents of which are incorporated by reference herein.

FIELD OF INVENTION

The present invention relates to process for the preparation of teneligliptin, 3-{(2S,4S)-4-[4-(3-methyl-1-phenyl-1H-pyrazol-5-yl)-1-piperazinyl]-2-pyrrolidinylcarbonyl}-1,3-thiazolidine and pharmaceutically acceptable salts thereof. The new process is directed to improvement in the manufacture of teneligliptin which would be industrially feasible and facilitate simple and cost effective manufacture of teneligliptin and salts thereof having better purity and yield.

BACKGROUND OF THE INVENTION

Teneligliptin which is chemically known as 3-{(2S,4S)-4-[4-(3-methyl-1-phenyl-1H-pyrazol-5-yl)-1-piperazinyl]-2-pyrrolidinylcarbonyl}-1,3-thiazolidine is represented structurally by a compound of formula (I):

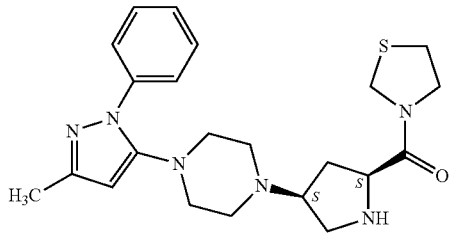

I

U.S. Pat. No. 7,074,794 (US'794) describes the process of preparation of trihydrochloride salt of compound I. The process described in the (US'794) employs diketene for the synthesis of tert-butyl-4-acetoacetylpiperazine-1-carboxylate which is one of the key intermediate in the synthesis of compound I from 1-tert-butyloxycarbonyl piperazine. There are several known drawbacks of the process which includes inter alia the instability of the diketene making it difficult to handle. Unfortunately, few alternatives are available for diketene reaction.

Thus, an object of the present invention is to provide a process to overcome aforesaid problems and to provide simple, cost effective and industrially feasible processes for manufacture of teneligliptin and pharmaceutically acceptable salt or solvate thereof. Teneligliptin and pharmaceutically acceptable salt or solvate thereof prepared by the process of present invention provides both enhanced yield and purity.

SUMMARY OF THE INVENTION

In one embodiment the present invention provides a process for the preparation of teneligliptin, a compound of formula I or salt or hydrate thereof comprising:

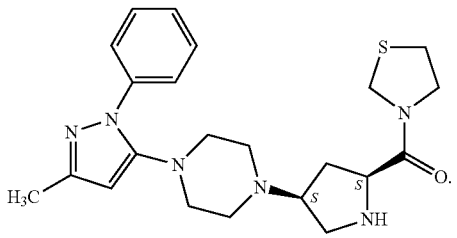

I a) reacting a compound of formula 11 with his (2-chloroethyl) amine or N-protected derivative or salt thereof,

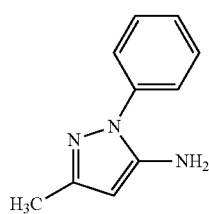

11

Or a) reacting 5-chloro-3-methyl-1-phenyl-1H-pyrazole-4-carbaldehyde, a compound of formula 30 with piperazine or N-protected derivative thereof,

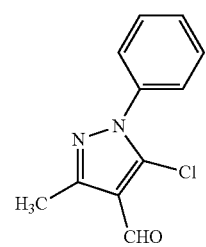

30

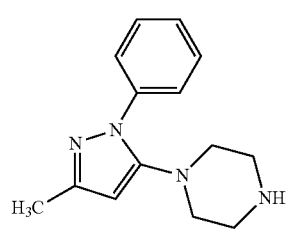

Int-B to obtain a compound of formula Int-B or an N-protected derivative or salt thereof;

b) reacting the compound of formula Int-B or N-protected derivative or salt thereof with a compound of formula 13 to obtain a compound of formula 14,

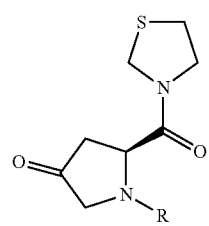

13

[Structure 14]

wherein R is an amino protecting group selected from the group consisting of aralkyl, acyl, lower alkoxycarbonyl, aralkyloxycarbonyl, lower alkanesulfonyl, aryl sulfonyl, tri-(loweralkyl)silyl, triphosgene; and c) deprotecting the compound of formula 14 to obtain teneligliptin, a compound of formula I or salt or hydrate thereof.

In one embodiment, the present invention provides amorphous teneligliptin.

In one embodiment, the present invention provides a process for preparation of teneligliptin 2.5 hydrobromide or a hydrate thereof comprising crystallizing teneligliptin 2.5 hydrobromide or a hydrate thereof from a solvent selected from methanol, n-butanol, tertiary butanol, N,N-dimethyl acetamide, N,N-dimethyl formamide, tetrahydrofuran, tetrahydropyran, 1,4-dioxane, propyl acetate, isopropyl acetate and methyl ethyl ketone, methyl isobutyl ketone and mixtures thereof.

In one embodiment, the present invention provides substantially pure teneligliptin 2.5 hydrobromide hydrate having a purity of at least 99% as measured by high performance liquid chromatography.

In one embodiment, the present invention provides a compound selected from the following;

[Structures 19, 20, 28, 29, 31, 32]

In one embodiment, the present invention provides teneligliptin 2.5 hydrobromide hydrate having less than 0.1% of any of the below compounds as measured by high performance liquid chromatography.

[Structures 29, 31]

-continued

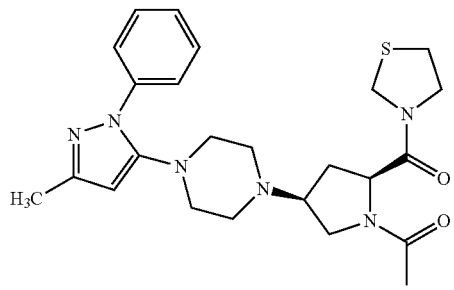
32

In one embodiment, the present invention provides use of bis (2-chloroethyl) amine or N-boc-bis(2-chloroethyl) amine or salt thereof in the preparation of compound of formula Int-B or teneligliptin.

In one embodiment, the present invention provides use of 5-chloro-3-methyl-1-phenyl-1H-pyrazole-4-carbaldehyde or tertiary-butyl-4-(4-formyl-3-methyl-1-phenyl-1H-pyrazol-5-yl) piperazine-1-carboxylate, in the preparation of compound of formula Int-B or teneligliptin.

BRIEF DESCRIPTION OF THE ACCOMPANYING FIGURES

FIG. 1: PXRD pattern of teneligliptin 2.5 hydrobromide hydrate, which is substantially in accordance with example 6.

Figure 2:
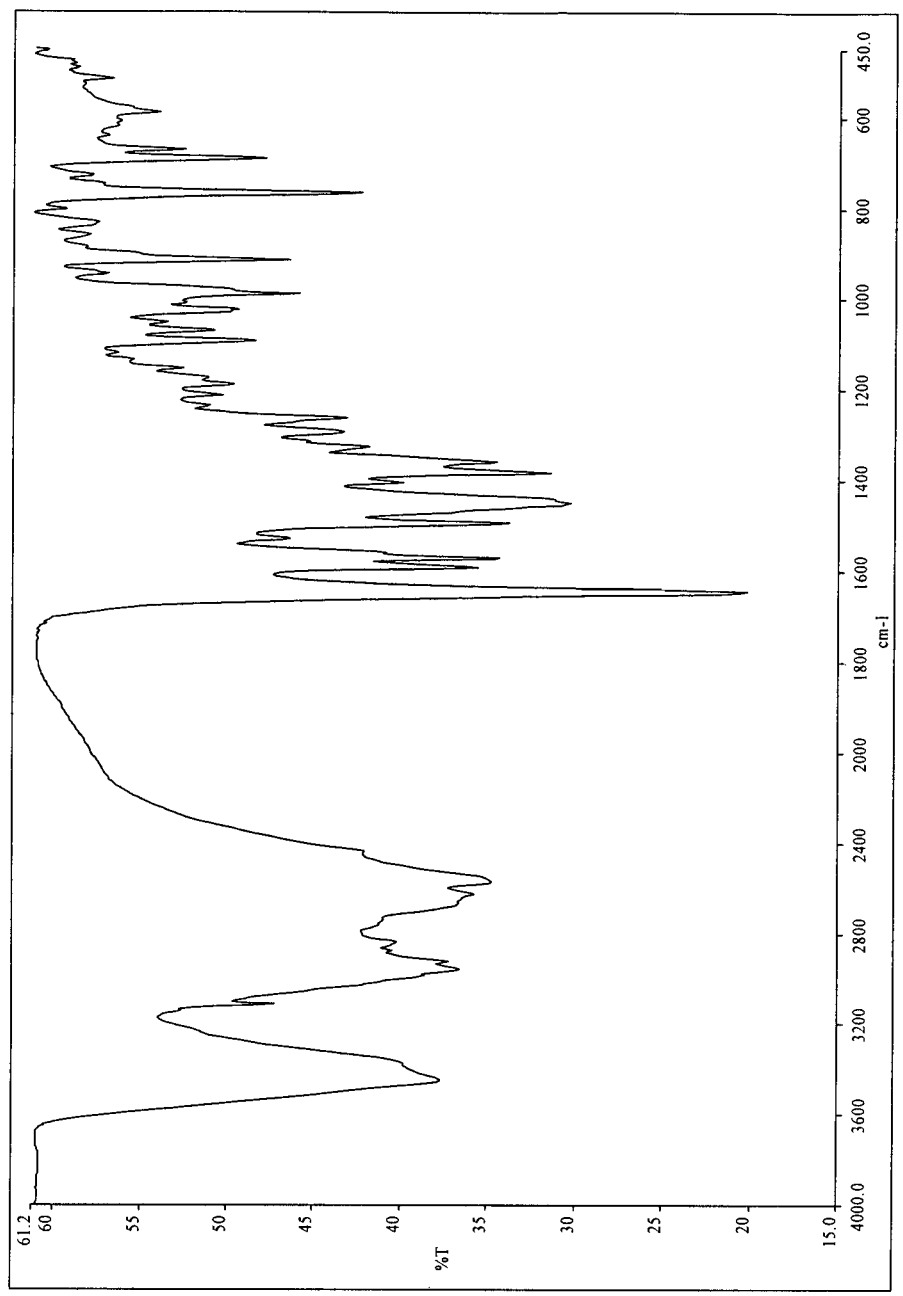

FIG. 2: IR pattern of teneligliptin 2.5 hydrobromide hydrate, which is substantially in accordance with example 6.

Figure 3:
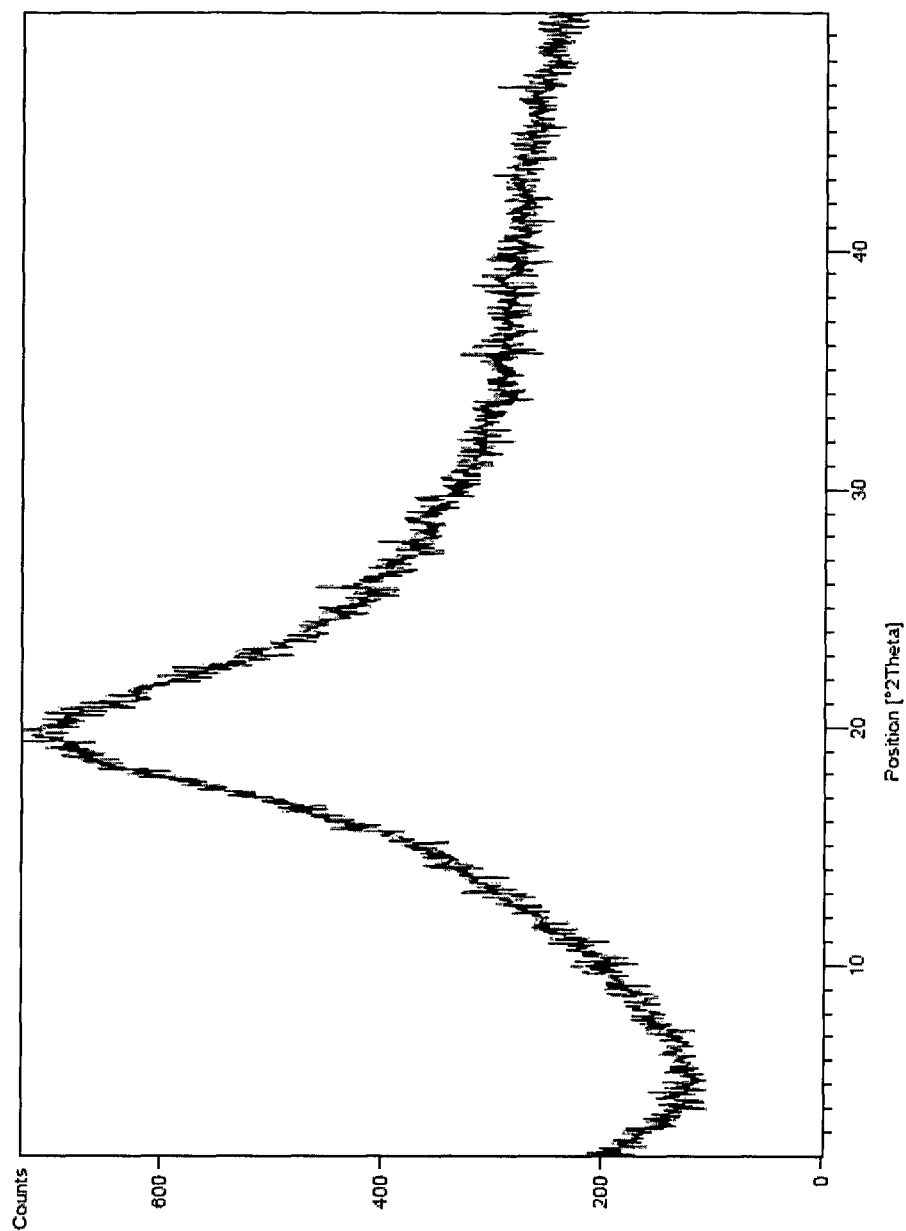

FIG. 3: PXRD pattern of teneligliptin, which is substantially in accordance with example 14 method A.

Figure 4:
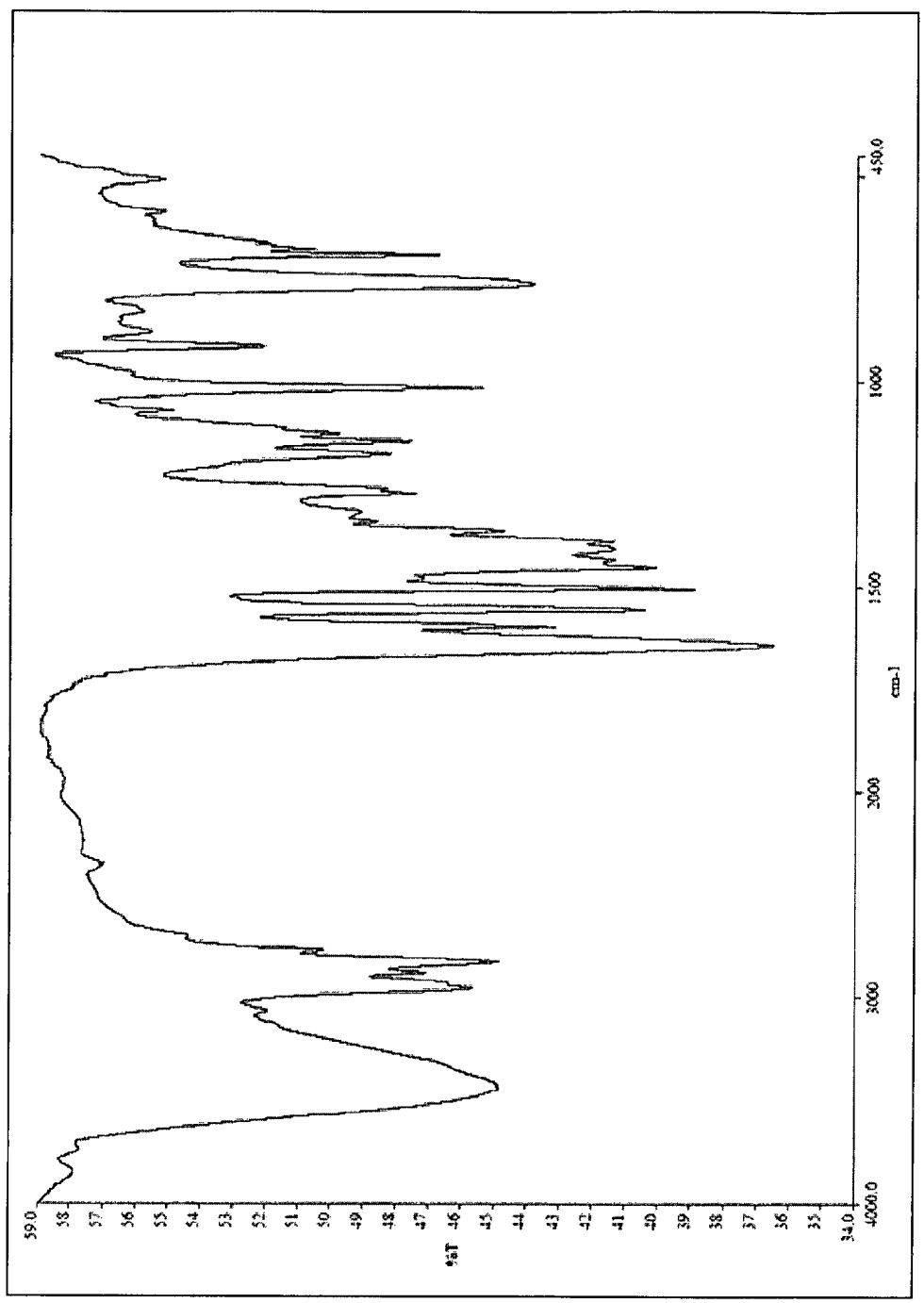

FIG. 4: IR pattern of teneligliptin which is substantially in accordance with example 14 method A.

Figure 5:
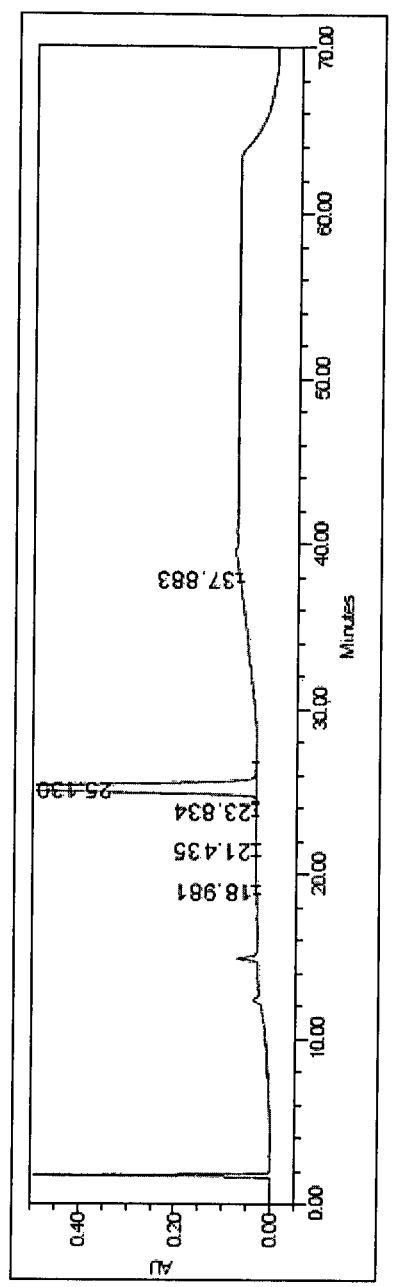

FIG. 5: HPLC chromatogram of teneligliptin 2.5 hydrobromide hydrate, which is substantially in accordance with example 6.

DETAILED DESCRIPTION OF THE INVENTION

In one embodiment, the present invention provides a process for the preparation of teneligliptin, a compound of formula I or salt or hydrate thereof comprising:

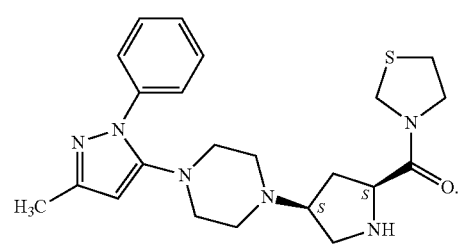
I a) reacting a compound of formula 11 with bis (2-chloroethyl) amine or N-protected derivative or salt thereof,

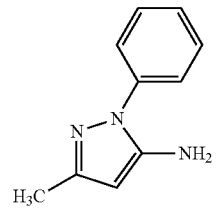
11

Or a) reacting 5-chloro-3-methyl-1-phenyl-1H-pyrazole-4-carbaldehyde, a compound of formula 30 with piperazine or N-protected derivative thereof,

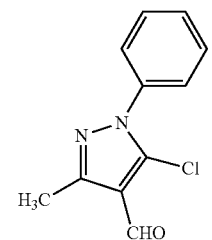
30

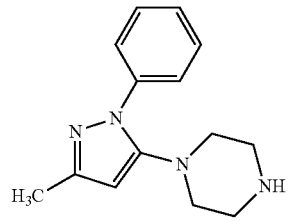
Int-B to obtain a compound of formula Int-B or an N-protected derivative or salt thereof;

b) reacting the compound of formula Int-B or an N-protected derivative or salt thereof with a compound of formula 13 to obtain a compound of formula 14,

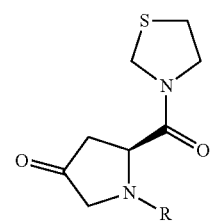
13

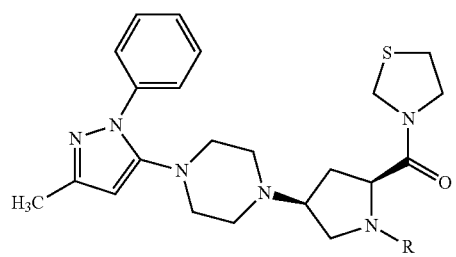
14 wherein R is an amino protecting group selected from the group consisting of aralkyl, acyl, lower alkoxycarbonyl, aralkyloxycarbonyl, lower alkanesulfonyl, aryl sulfonyl, tri-(loweralkyl)silyl, triphosgene; and c) deprotecting the compound of formula 14 to obtain teneligliptin, a compound of formula I or salt or hydrate thereof.

In one embodiment, in a) of the above process a compound of formula 11 reacts with bis (2-chloroethyl) amine or an N-protected derivative or salt thereof in a suitable solvent and in presence of a suitable base to obtain a compound of formula Int-B or derivative or salt thereof.

The term "N-protected derivative" is intended to mean an amino protecting group selected from the group consisting of aralkyl, acyl, lower alkoxycarbonyl, aralkyloxycarbonyl, lower alkanesulfonyl, aryl sulfonyl, and tri-(loweralkyl) silyl. The preferred amino protecting group is lower alkoxy carbonyl like tert-butoxycarbonyl.

A suitable base may be selected from organic or an inorganic base. The inorganic base may be selected from, but is not limited to hydroxides such as sodium hydroxide, potassium hydroxide; carbonates such as sodium carbonate, potassium carbonate; bicarbonates such as sodium bicarbonate, potassium bicarbonate, hydrides such as sodium hydride, alkoxides such as sodium methoxide, potassium methoxide, potassium tert-butoxide; while the organic base may be selected from, but is not limited to (R)-(+)-2,2'-Bis (diphenylphosphino)-1,1'-binaphthyl, triethyl amine, trimethyl amine, pyridine, diisopropyl amine and dimethyl amino pyridine. Preferably, the base is sodium hydride.

A suitable solvent may be selected from, but is not limited to halogenated hydrocarbons such as methylene chloride, ethylene chloride, chloroform and carbon tetrachloride; alcohols such as methanol, ethanol, 1-propyl alcohol, 2-propanol, tert-butanol; esters such as ethyl acetate, isopropyl acetate and butyl acetate; amides such as formamide, N,N-dimethylformamide, N,N-dimethylacetamide; dimethyl sulfoxide; nitrile such as acetonitrile, propionitrile; ethers such as diethyl ether, diisopropyl ether, t-butyl methyl ether, 1,4-dioxane, tetrahydrofuran; hydrocarbons such as benzene, toluene, cyclohexane, methyl cyclohexane and toluene; or mixtures thereof. Preferably, the solvent is N,N-dimethylformamide.

In one embodiment, the present invention relates to a process for the preparation of a salt of Int-B comprising reacting compound of formula Int-B with a suitable acid.

A suitable acid may be selected from the group consisting of acetic acid, trifluoroacetic acid, hydrochloric acid, hydrobromic acid, nitric acid, oxalic acid, malonic acid, succinic acid, phosphoric acid, maleic acid, naphthalene-1-sulfonic acid, naphthalene-2-sulfonic acid, gallic acid, (+)camphorsulfonic acid, (−)camphorsulfonic acid, fumaric acid, L-tartaric acid, ethanedisulfonic acid, citric acid, oxalic acid, mallonic acid, mallic acid, sulphuric acid, hydrochloric acid, p-toluene sulphonic acid, methane sulfonic acid, besyl acid and the like. Preferably, the acetate salt of compound of formula Int-B is prepared.

In one embodiment, a compound of formula 11 in N,N-dimethylformamide is reacted with bis (2-chloroethyl) amine or N-protected derivative or salt thereof in the presence of sodium hydride. The reaction is carried out at a temperature of about 25 to about 35° C. Preferably, the reaction transpires at about 20 to about 30° C. Compound of formula Int-B thus formed is further reacted with acetic acid in a suitable solvent. The acetate salt of compound of formula Int-B is isolated by known methods in the art for example filtration and centrifugation.

A suitable solvent for the preparation of salt of compound of formula Int-B may be selected from, but is not limited to halogenated hydrocarbons such as methylene chloride, ethylene chloride, chloroform and carbon tetrachloride; alcohols such as methanol, ethanol, 1-propyl alcohol, 2-propanol, tert-butanol; esters such as ethyl acetate, isopropyl acetate and butyl acetate; amides such as formamide, N,N-dimethylformamide, N,N-dimethylacetamide; nitrile such as acetonitrile, propionitrile; ethers such as diethyl ether, diisopropyl ether, t-butyl methyl ether, 1,4-dioxane, tetrahydrofuran; hydrocarbons such as benzene, toluene, cyclohexane, methyl cyclohexane; or mixtures thereof. Preferably, the solvent is toluene.

In one embodiment, in a) of the above process 5-chloro-3-methyl-1-phenyl-1H-pyrazole-4-carbaldehyde, a compound of formula 30 is reacted with piperazine or N-protected derivative thereof to obtain a compound of formula Int-B or an N-protected derivative or salt thereof.

The reaction may be carried out in presence of a suitable solvent and a base.

The solvent may be selected from, but is not limited to halogenated hydrocarbons such as methylene chloride, ethylene chloride, chloroform and carbon tetrachloride; alcohols such as methanol, ethanol, 1-propyl alcohol, 2-propanol, tert-butanol; esters such as ethyl acetate, isopropyl acetate and butyl acetate; amides such as formamide, N,N-dimethylformamide, N,N-dimethylacetamide; nitrile such as acetonitrile, propionitrile; ethers such as diethyl ether, diisopropyl ether, t-butyl methyl ether, 1,4-dioxane, tetrahydrofuran; hydrocarbons such as benzene, toluene, cyclohexane, methyl cyclohexane; or mixtures thereof Preferably, the solvent is N,N-dimethyl formamide.

A suitable base may be selected from organic or an inorganic base. The inorganic base may be selected from, but is not limited to hydroxides such as sodium hydroxide, potassium hydroxide; carbonates such as sodium carbonate, potassium carbonate; bicarbonates such as sodium bicarbonate, potassium bicarbonate, hydrides such as sodium hydride, alkoxides such as sodium methoxide, potassium methoxide, potassium tert-butoxide; while the organic base may be selected from, but is not limited to (R)-(+)-2,2'-Bis (diphenylphosphino)-1,1'-binaphthyl, triethyl amine, trimethyl amine, pyridine, diisopropyl amine and dimethyl amino pyridine. Preferably, the base is potassium carbonate.

In one embodiment, 5-chloro-3-methyl-1-phenyl-1H-pyrazole-4-carbaldehyde, a compound of formula 30 is reacted with piperazine-1-carboxylic acid tert-butyl ester to obtain tert-butyl-4-(4-formyl-3-methyl-1-phenyl-1H-pyrazol-5-yl)piperazine-1-carboxylate, a compound of formula 31

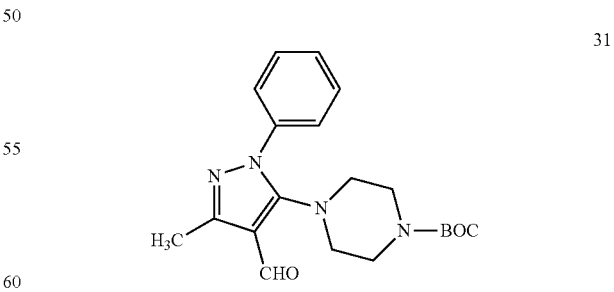

which is further converted to compound of formula Int-B.

The reaction transpires over a temperature range of about 25 to 200° C. Preferably, the reaction transpires at about 120-140° C.

In one embodiment, 5-chloro-3-methyl-1-phenyl-1H-pyrazole-4-carbaldehyde, a compound of formula 30 is reacted with piperazine-1-carboxylic acid tert-butyl ester in presence of dimethyl formamide and potassium carbonate to obtain tert-butyl-4-(4-formyl-3-methyl-1-phenyl-1H-pyrazol-5-yl)piperazine-1-carboxylate, a compound of formula 31.

The tert-butyl-4-(4-formyl-3-methyl-1-phenyl-1H-pyrazol-5-yl)piperazine-1-carboxylate, compound of formula 31, is converted to 1-(3-methyl-1-phenyl-1H-5yl)piperazine.

The conversion may be carried out by reacting with an acid selected from the group consisting of hydrochloric acid, trifluoroacetic acid, sulphuric acid, hydrobromic acid, p-toluene sulfonic acid, boron tribromide, formic acid. Preferably, the acid is para-toluene sulfonic acid.

The conversion may be carried out in an inert solvent or without solvent. Inert solvent may be selected from water, alcohols such as methanol, ethanol, 1-propanol, 2-propanol, tertiary-butanol; ketones such as acetone, methyl ethyl ketone; nitriles such as acetonitrile, propionitrile; amides such as formamide, N,N-dimethylformamide, N,N-dimethylacetamide, 1,3-dimethyl-2-imidazolidinone; ethers such as diethyl ether, diisopropyl ether, t-butyl methyl ether, 1,4-dioxane, tetrahydropyran, tetrahydrofuran; esters such as ethyl formate, ethyl acetate, propyl acetate; halogenated hydrocarbons such as methylenedichloride, chloroform, 1,2-dichloroethane; hydrocarbons such as n-hexane, cyclohexane, benzene, toluene and methyl cyclohexane; sulfoxides such as dimethyl sulfoxide; polar solvents such as sulfolane, hexamethylphosphorylamide; or mixtures thereof. Preferably, the solvent is methanol.

In one embodiment, tert-butyl-4-(4-formyl-3-methyl-1-phenyl-1H-pyrazol-5-yl)piperazine-1-carboxylate, compound of formula 31 is treated with para-toluene sulfonic acid in methanol to obtain compound of formula Int-B.

The conversion may transpire at a temperature of about 0 to about 100° C. Preferably, the reaction transpires at about 75 to about 80° C.

In one embodiment, in b) of the above process the compound of formula Int-B or N-protected derivative or salt thereof is reacted with a compound of formula 13 to obtain a compound of formula 14.

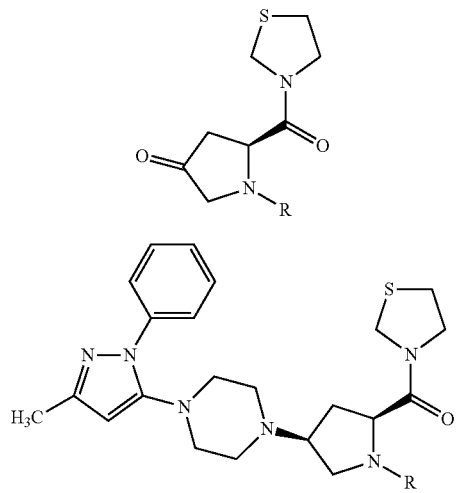

In one embodiment, the above process is carried out in presence of a suitable solvent and a reducing agent to obtain a compound of formula 14.

A suitable solvent may be selected from, but is not limited to halogenated hydrocarbons such as methylene chloride, ethylene chloride, chloroform and carbon tetrachloride; alcohols such as methanol, ethanol, 1-propyl alcohol, 2-propanol, tert-butanol; esters such as ethyl acetate, isopropyl acetate and butyl acetate; amides such as formamide, N,N-dimethylformamide, N,N-dimethylacetamide; nitrile such as acetonitrile, propionitrile; ethers such as diethyl ether, diisopropyl ether, t-butyl methyl ether, 1,4-dioxane, tetrahydrofuran, tetrahydropyran; hydrocarbons such as benzene, toluene, cyclohexane, methyl cyclohexane; or mixtures thereof. Preferably, the solvent is methylenedichloride.

A suitable reducing agent may be selected from borohydrides such as sodium borohydride, potassium borohydride, sodium cyanoborohydride, sodium triacetoxy borohydride; hydride such as lithium hydride and lithium aluminium hydride. Preferably, the reducing agent is sodium triacetoxy borohydride.

The amino protecting group represented by R in compound of formula 13 and 14 may be selected from the group consisting of aralkyl such as benzyl, p-nitrobenzyl, benzhydryl, trityl; acyl such as formyl, acetyl, propionyl, methoxyacetyl, methoxypropionyl, benzoyl, thienylacetyl, thiazolylacetyl, tetrazolylacetyl, thiazolylglyoxyloyl, thienylglyoxyloyl; lower alkoxy-carbonyl such as methoxycarbonyl, ethoxycarbonyl, tert-butoxycarbonyl; aralkyloxycarbonyl such as benzyloxycarbonyl, p-nitrobenzyloxycarbonyl, 9-fluorenylmethyloxycarbonyl; lower alkane sulfonyl such as methane sulfonyl, ethane sulfonyl; aryl sulfonyl such as toluene sulfonyl; tri-(lower alkyl) silyl such as trimethylsilyl; and triphosgene.

In one embodiment, in step b) when R is acetyl, the process comprises reacting (5S)-1-acetyl-5-(1,3-thiazolidin-3-carbonyl) pyrrolidin-3-one, a compound of formula 29

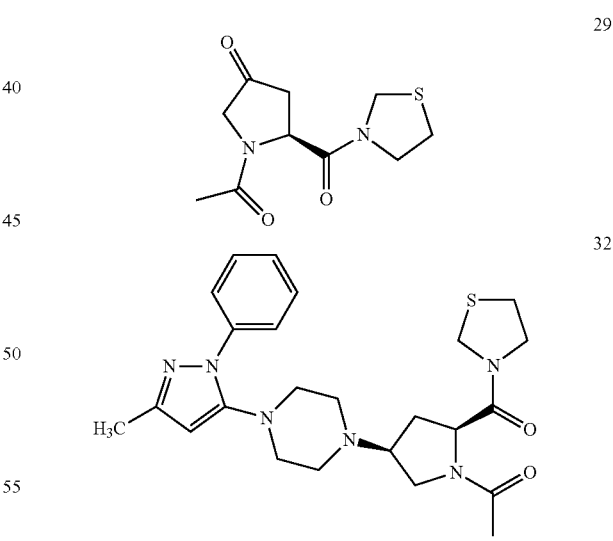

with a compound of formula Int-B to obtain 1-[(2S, 4S)-4-[4-(3-methyl-1-phenyl-1H-pyrazol-5-yl)piperazin-1-yl]-thiazolidin-3-ylcarbonyl)pyrrolidin-1-yl]ethanone, a compound of formula 32.

In one embodiment, in step b) when R is 9-fluoroenylmethyloxycarbonyl (Fmoc), the process comprises reacting 9H-fluoren-9-ylmethyl (2S)-4-oxo-2-(1,3-thiazolidin-3-ylcarbonyl)pyrrolidine-1-carboxylate, compound of formula 19

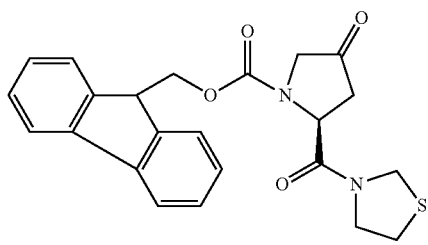

19

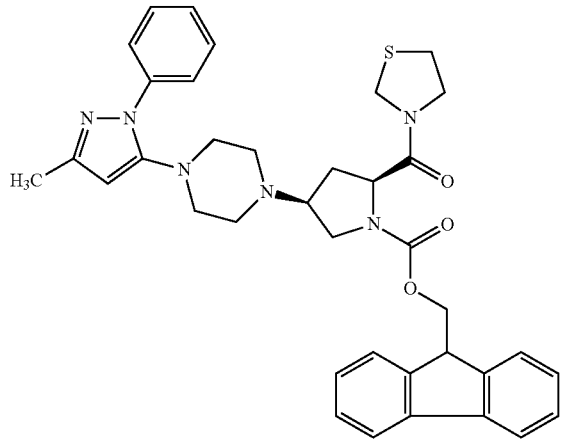

20 with a compound of formula Int-B to obtain 3-{(2S,4S)-1-9H-fluoren-9-ylmethoxycarbonyl-4-[4-(3-methyl-1-phenyl-5-pyrazolyl)-1-piperazinyl]-2-pyrrolidinylcarbonyl}-1,3-thiazolidine, compound of formula 20.

In one embodiment, in step b) R is benzyl, the process comprises reacting 1-benzyl (2S)-4-oxo-2-(1,3-thiazolidin-3-ylcarbonyl)pyrrolidine compound of formula 15 with a compound of formula Int-B

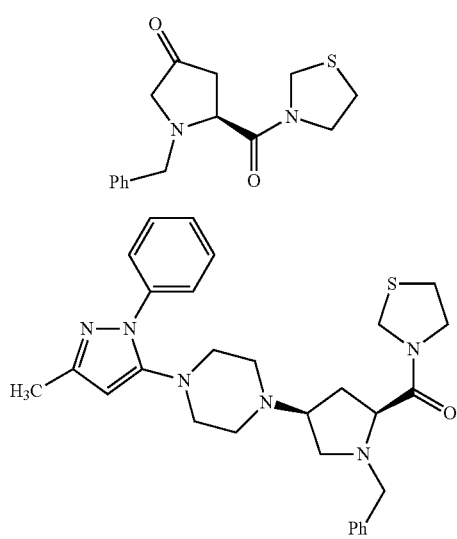

15

16 to obtain 3-{(2S,4S)-1-benzyl-4-[4-(3-methyl-1-phenyl-5-pyrazolyl)-1-piperazinyl]-2-pyrrolidinylcarbonyl}-1-,3-thiazolidine, compound of 16.

In one embodiment, in step b) R is benzyloxy carbonyl, the process comprises reacting benzyloxycarbonyl-(2S)-4-oxo-2-(1,3-thiazolidin-3-ylcarbonyl)pyrrolidine-1-carboxylate, compound of formula 21 with a compound of formula Int-B

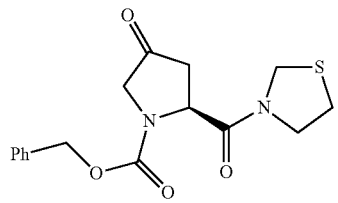

21

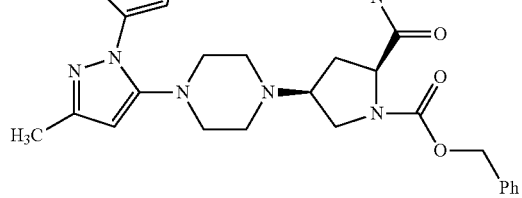

22 to obtain 3-{(2S,4S)-1-benzyloxycarbonyl-4-[4-(3-methyl-1-phenyl-5-pyrazolyl)-1-piperazinyl]-2-pyrrolidinylcarbonyl}-1,3-thiazolidine, compound of 22.

In one embodiment, in step b) R is triphenyl methyl, the process comprises reacting 1-trityl-(2S)-4-oxo-2-(1,3-thiazolidin-3-ylcarbonyl) pyrrolidine, compound of formula 17 with a compound of formula Int-B

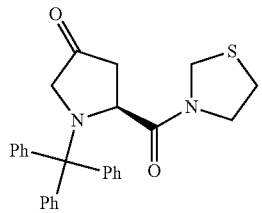

17

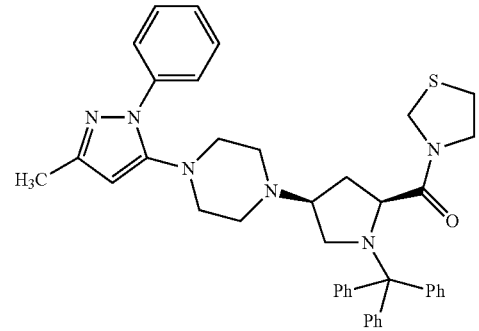

18 to obtain 3-{(2S,4S)-1-trityl-4-[4-(3-methyl-1-phenyl-5-pyrazolyl)-1-piperazinyl]-2-pyrrolidinylcarbonyl}-1,3-thiazolidine, compound of 18.

In one embodiment, in step b) R is trichloromethoxy carbonyl, the process comprises reacting trichloromethoxycarbonyll (2S)-4-oxo-2-(1,3-thiazolidin-3-ylcarbonyl)pyrrolidine-1-carboxylate, compound of formula 23 with a compound of formula Int-B

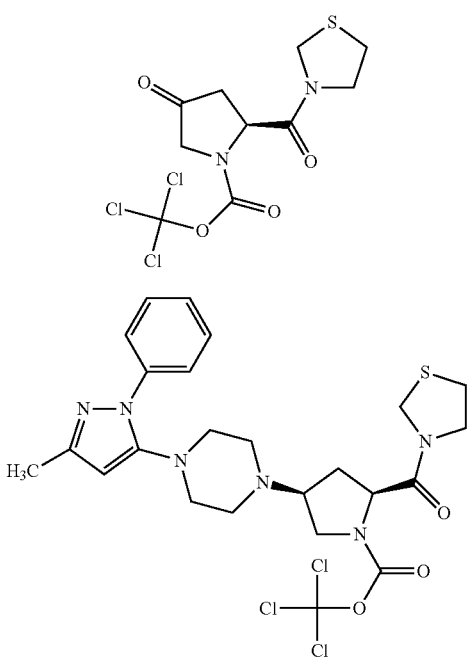

to obtain 3-{(2S,4S)-1-trichloromethoxycarbonyl-4-[4-(3-methyl-1-phenyl-5-pyrazolyl)-1-piperazinyl]-2-pyrrolidinylcarbonyl}-1-,3-thiazolidine, compound of 24.

In one embodiment, in c) of the above process compound of formula 14 is deprotected using suitable reagents to obtain teneligliptin, a compound of formula I or a salt or hydrate thereof.

Suitable reagents, depending on the type of protective group, may be selected from the group consisting of acid like hydrochloric acid, trifluoroacetic acid, hydrobromic acid, sulphuric acid, hydrobromic acid, p-toluene sulfonic acid, boron tribromide, formic acid; reduction using palladium/carbon, palladium acetate or palladium hydroxide, base such as piperidine, ammonia, methylamine and cyclohexyl amine.

The deprotection reaction may be carried out in an inert solvent or without solvent. The inert solvent may be selected from water, alcohols such as methanol, ethanol, 1-propanol, 2-propanol, tertiary-butanol; ketones such as acetone, methyl ethyl ketone; nitriles such as acetonitrile, propionitrile; amides such as formamide, N,N-dimethylformamide, N,N-dimethylacetamide, 1,3-dimethyl-2-imidazolidinone; ethers such as diethyl ether, diisopropyl ether, t-butyl methyl ether, 1,4-dioxane, tetrahydrofuran, tetrahydropyran; esters such as ethyl formate, ethyl acetate, propyl acetate; halogenated hydrocarbons such as dichloromethane, chloroform, methylene dichloride; hydrocarbons such as n-hexane, cyclohexane, benzene, toluene and methyl cyclohexane; sulfoxides such as dimethyl sulfoxide; polar solvents such as sulfolane, hexamethylphosphorylamide; or mixtures thereof.

In one embodiment, in step c) when R is acetyl the process comprises deprotecting 1-[(2S,4S)-4-[4-(3-methyl-1-phenyl-1H-pyrazol-5-yl)piperazin-1-yl]-2-(1,3-thiazolidin-3-ylcarbonyl)pyrrolidin-1-yl]ethanone, the compound of formula 32 with an inorganic acid selected from the group consisting of hydrochloric acid, hydrobromic acid, sulfuric acid, phosphoric acid; inorganic base selected from the group consisting of sodium hydroxide, potassium hydroxide, sodium carbonate, potassium carbonate and the like to obtain teneligliptin, compound of formula I or salt or hydrate thereof.

In one embodiment, 1-[(2S,4S)-4-[4-(3-methyl-1-phenyl-1H-pyrazol-5-yl)piperazin-1-yl]-2-(1,3-thiazolidin-3-ylcarbonyl)pyrrolidin-1-yl]ethanone, the compound of formula 32 is deprotected using aqueous hydrobromic acid in 2-propanol.

The deprotection reaction transpires at a temperature of about 0 to 120° C. Preferably, at a temperature of about 80-85° C.

In one embodiment, in step c) when R is 9-fluorenylmethyloxycarbonyl (Fmoc), 3-{(2S,4S)-1-9H-fluoren-9-yl-methoxycarbonyl-4-[4-(3-methyl-1-phenyl-5-pyrazolyl)-1-piperazinyl]-2-pyrrolidinyl carbonyl}-1-,3-thiazolidine, compound of formula 20 is deprotected using a suitable base selected from the group consisting of inorganic or organic base. Organic base may be selected from dimethyl amino pyridine, diisopropyl amine, pyridine, piperidine, triethyl amine, trimethyl amine and the like. Preferably, the base is piperidine.

The deprotection reaction transpires at a temperature of about 0 to 120° C. Preferably, at a temperature of about 80 to about 85° C.

In one embodiment, the present invention provides a process for the preparation of teneligliptin, a compound of formula I or salt thereof, comprising:
a) reacting compound of formula Int-B or N-protected derivative or salt thereof with a compound of formula 29 to obtain a compound of formula 32; and
b) deprotecting compound of formula 32 to obtain teneligliptin, a compound of formula I or salt thereof.

In one embodiment, in a) of the above step, compound of formula 29 is reacted with compound of formula Int-B to obtain a compound of formula 32.

The reaction may be carried out in presence of a suitable reducing agent as discussed above.

The reaction transpires over a period of about 3 to 15 hours. Preferably the reaction transpires over a period of about 4 to 5 hours. The compound of formula 31 is isolated by methods known in the art such as filtration, concentration and the like.

In one embodiment, in step b) of the above process the teneligliptin is obtained by deprotecting compound of formula 32 as discussed above.

In one embodiment, the present invention provides amorphous teneligliptin.

In one embodiment, the present invention provides amorphous teneligliptin characterized by $^1$H NMR (300 MHz, DMSO-$D_6$) having peaks at 1.55, 2.14, 2.2-2.22, 2.43-2.76, 2.92-3.07, 3.63-3.84, 4.42-4.66 , 5.78 , 7.24-7.29, 7.43-7.47, 7.72-7.75.

In one embodiment, the present invention provides amorphous teneligliptin characterized by IR peaks at about 3443.97, 2952.9, 2826.5, 1639.5, 1556.4, 1504.5, 1016.23, 915.9, 764.18 cm$^{-1}$.

In one embodiment, the present invention provides teneligliptin, which is substantially in accordance with FIG. 3.

In one embodiment, the present invention provides teneligliptin, which is substantially in accordance with FIG. 4.

In one embodiment, the present invention provides crystalline teneligliptin.

In one embodiment, the present invention provides a process for the purification of teneligliptin without column chromatography comprising treating teneligliptin with a solvent selected from the group consisting of alcohols, ethers, esters, amides, nitriles, sulfoxides, ketones, hydrocarbons, acetates, halogenated hydrocarbons, water or mixtures thereof.

In one embodiment, the present invention provides a process for the purification of teneligliptin comprising treating teneligliptin with a mixture of ester and an alcohol.

In one embodiment, the present invention provides a process for the purification of teneligliptin comprising treating teneligliptin with 1-propanol.

In one embodiment, the present invention provides teneligliptin, having a purity of about 99% and above as measured by HPLC (high performance liquid chromatography).

The salt of compound of formula I can be prepared by methods known in the art. For example, the salt of the present invention can be obtained by reacting compound of formula I with an organic acid or inorganic acid selected from the group consisting of hydrochloric acid, sulfuric acid, acetic acid, trifuoroacetic acid, hydrobromic acid, nitric acid, mesyl acid, maleic acid, tosyl acid, besyl acid, naphthalene-1-sulfonic acid, naphthalene-2-sulfonic acid, gallic acid, (+)-camphorsulfonic acid, (−)-camphorsulfonic acid, fumaric acid, sulfuric acid, succinic acid, L-tartaric acid, ethanedisulfonic acid, citric acid, oxalic acid, malic acid, maleic acid, malonic acid, and phosphoric acid. Preferably, a hydrobromide salt of compound of formula I is prepared.

In one embodiment, a salt of compound of formula I may be prepared in presence of suitable solvent. The suitable solvent may be selected from the group consisting of methanol, n-butanol, tertiary butanol, propyl acetate, butyl acetate, ethers such as tetrahydrofuran, tetrahydropyran, diethyl ether, diisopropyl ether, methyl tertiary butyl ether; ketones such as acetone, methyl ethyl ketone, amide as such as N,N-dimethyl formamide, N,N-dimethyl acetamide; nitriles such as acetonitrile, hydrocarbons such as toluene, xylene, cyclohexane, methyl cylcohexane; halogenated hydrocarbons such as methylene dichloride, chloroform, ethylene dichloride. Preferably, the solvent is a mixture of a methanol and tertiary butanol.

In one embodiment, the present invention provides a process for preparation of teneligliptin 2.5 hydrobromide or a hydrate thereof which comprises treating teneligliptin with hydrobromic acid or hydrobromic acid in acetic acid in a solvent selected from methanol and tertiary butanol.

In one embodiment, teneligliptin is dissolved in a mixture of methanol and tertiary butanol. The solution is heated to a temperaturte of about 30° C. to about reflux temperature of the solvent mixture. Preferably the solution is heated to about 70-75° C. Aqueous hydrobromic acid is added to the solution at this temperature. The reaction mixture is cooled to a temperature of about −5 to about 25° C. Teneligliptin 2.5 hydrobromide hydrate is isolated by known methods in the art such as filtration, centrifugation and the like.

In one embodiment, the present invention provides a process for the preparation of teneligliptin 2.5 hydrobromide hydrate comprising crystallising teneligliptin 2.5 hydrobromide hydrate from a solvent selected from the group consisting of methanol, n-butanol, tertiary butanol, propyl acetate, isopropyl acetate, butyl acetate, ethers such as diethyl ether, tetrahydrofuran, tetrahydropyran, diisopropyl ether, methyl tertiary butyl ether; ketones such as acetone, methyl ethyl ketone, amide as such as N,N-dimethyl formamide, N,N-dimethyl acetamide; nitriles such as acetonitrile, hydrocarbons such as toluene, xylene, cyclohexane, methyl cylcohexane; halogenated hydrocarbons such as methylene dichloride, chloroform, ethylene dichloride and mixtures thereof. Preferably, the solvent is methanol or a mixture of a methanol and tertiary-butanol.

In one embodiment, the present invention provides a process for the preparation of teneligliptin 2.5 hydrobromide hydrate comprising crystallising teneligliptin 2.5 hydrobromide hydrate from methanol and n-butanol.

In one embodiment, the present invention provides a process for the preparation of teneligliptin 2.5 hydrobromide hydrate comprising crystallising teneligliptin 2.5 hydrobromide hydrate from N,N-dimethyl acetamide and tetrahydrofuran.

In one embodiment, the present invention provides a process for the preparation of teneligliptin 2.5 hydrobromide hydrate comprising crystallising teneligliptin 2.5 hydrobromide hydrate from N,N-dimethyl formamide and tetrahydrofuran.

In one embodiment, the present invention provides a process for the preparation of teneligliptin 2.5 hydrobromide hydrate comprising crystallising teneligliptin 2.5 hydrobromide from methanol.

In one embodiment, teneligliptin 2.5 hydrobromide hydrate is contacted with methanol and the reaction mixture is heated to reflux to obtain a solution. The solution may be treated with charcoal and filtered hot through a celite bed. The reaction mixture is cooled to a temperature of about 15-20° C. and pure teneligliptin 2.5 hydrobromide hydrate is isolated.

In one embodiment, the present invention provides process of purification of teneligliptin 2.5 hydrobromide hydrate by solvent/anti-solvent method.

In one embodiment, the present invention provides substantially pure teneligliptin 2.5 hydrobromide having a purity of at least 99% as measured by high performance liquid chromatography.

In one embodiment, the present invention provides substantially pure teneligliptin 2.5 hydrobromide hydrate having a purity of at least 99.7% as measured by high performance liquid chromatography.

In one embodiment, the present invention provides substantially pure teneligliptin 2.5 hydrobromide hydrate having a purity of at least 99.9% as measured by high performance liquid chromatography.

In one embodiment, the present invention provides substantially pure teneligliptin 2.5 hydrobromide hydrate, which is substantially in accordance with FIG. 1.

In one embodiment, the present invention provides substantially pure teneligliptin 2.5 hydrobromide hydrate, which is substantially in accordance with FIG. 2

In one embodiment, the present invention provides teneligliptin or salt or solvate thereof having less than about 0.2% of (2S,4R) isomer of teneligliptin or a salt or solvate thereof, having less than about 0.15% of (2S, 4R) isomer of teneligliptin or a salt or solvate thereof, having less than about 0.1% of (2S, 4R) isomer of teneligliptin or a salt or solvate hereof as measured by chiral chromatography. Preferably, (2S, 4R) isomer of teneligliptin or a salt or solvate thereof is not detected in teneligliptin or a salt or solvate thereof In one embodiment, the present invention provides teneligliptin or salt or solvate thereof having less than about 0.2% of (2R,4S) isomer of teneligliptin or a salt or solvate thereof, having less than about 0.15% of (2R,4S) isomer of teneligliptin or a salt or solvate thereof; having less than about 0.1% of (2R,4S) isomer of teneligliptin or a salt or solvate thereof as measured by chiral chromatography. Preferably, (2R,4S) isomer of teneligliptin or a salt or solvate thereof is not detected in teneligliptin or a salt or solvate thereof.

In one embodiment, the present invention provides teneligliptin or salt or solvate thereof thereof having less than about 0.2% of (2R,4R) isomer of teneligliptin or a salt or solvate thereof, having less than about 0.15% of (2R,4R) isomer of teneligliptin or a salt or solvate thereof, having less than about 0.1% of (2R,4R) isomer of teneligliptin or a salt or solvate thereof as measured by chiral chromatography. Preferably, (2R, 4R) isomer of teneligliptin or a salt or solvate thereof is not detected in teneligliptin or a salt or solvate thereof.

In one embodiment, the present invention provides teneligliptin or salt or solvate thereof having chemical purity not less than about 99.5% as measured by HPLC (high performance liquid chromatography) and chiral purity of about 100% as measured by chiral chromatography.

In one embodiment, the present provides compound of formula 19.

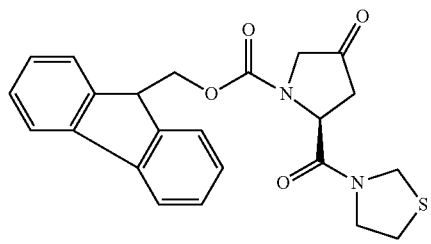

19

In one embodiment, the present invention provides compound of formula 19 characterized by ¹H NMR (300 MHz, DMSO-d6) peaks at 2.43, 2.96-3.12 , 3.60-3.95, 4.19-4.36, 4.41-4.63, 4.75-4.83, 5.02-5.11, 7.31-7.44, 7.58-7.67, 7.89-7.91.

In one embodiment, the present invention provides compound of formula 20

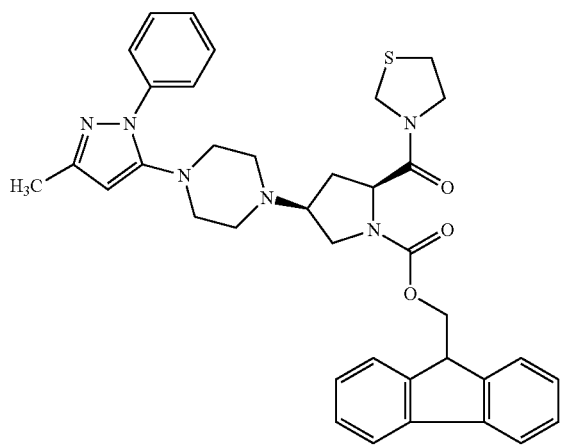

20

In one embodiment, the present invention provides compound of formula 20 characterized by ¹H NMR (300 MHz, DMSO-d6) peaks at 2.14 , 2.40 , 2.73-3.08 , 3.24-3.34, 3.47-3.82, 4.15-4.69 , 5.78 , 7.27-7.60 , 7.62-7.67, 7.72-7.69, 7.87-7.89.

In one embodiment, the present invention provides compound of formula 28

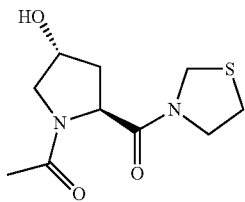

28

In one embodiment, the present invention provides compound of formula 28 characterised by ¹H NMR (300 MHz, DMSO-d6) peaks at 2.07, 2.19-2.30, 3.31, 3.50-3.53, 3.79-3.84, 4.18-4.21, 4.49-4.77.

In one embodiment, the present invention provides compound of formula 29.

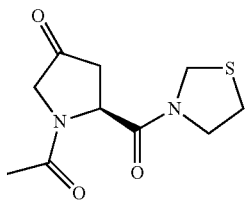

29

In one embodiment, the present invention provides compound of formula 29 characterised by ¹H NMR (300 MHz, CDCl₃) peaks at 1.98, 2.91-3.00, 3.09-3.12, 3.59-3.63, 3.92-3.98, 4.10-4.16, 4.431-4.35, 4.40-4.50, 4.62-4.65, 4.91-4.94, 5.10-5.18.

In one embodiment, the present invention provides compound of formula 31.

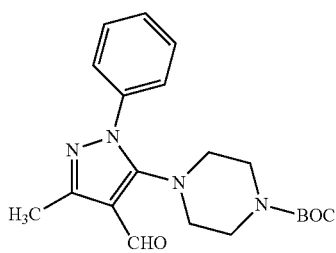

31

In one embodiment, the present invention provides compound of formula 31 characterised by ¹H NMR (300 MHz, CDCl₃) peaks at 9.94, 7.29-7.46, 3.4, 3.07, 2.4, 1.4.

In one embodiment, the present invention provides compound of formula 32.

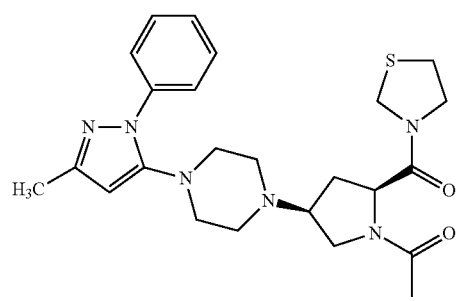

32

In one embodiment, the present invention provides compound of formula 32 characterised by ¹H NMR (300 MHz, DMSO-D₆) peaks at 1.48-1.52, 1.94, 2.14, 2.5-2.78, 2.88-3.2, 3.6-4.79, 5.79, 7.27, 7.45, 7.77.

In one embodiment, the present invention provides teneligliptin 2.5 hydrobromide hydrate having less than 0.1% of any of the below compounds

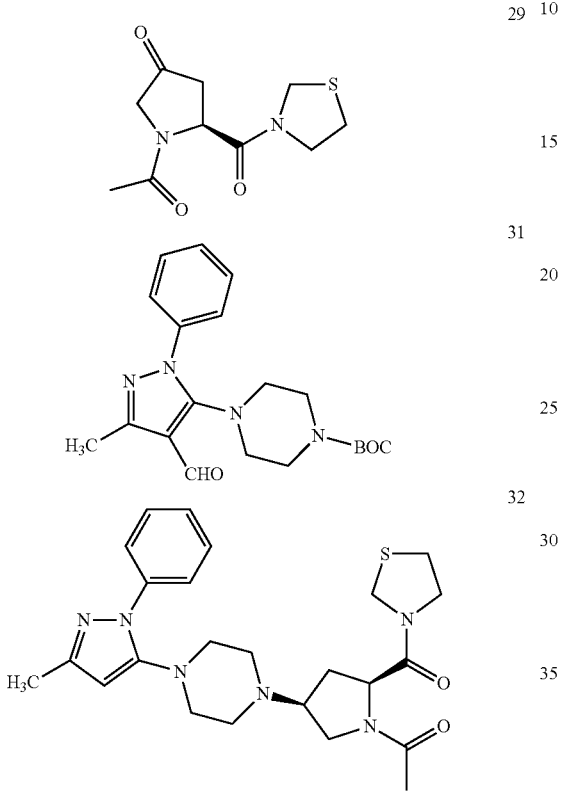

In one embodiment, the present invention provides use of bis (2-chloroethyl) amine or N-boc-bis(2-chloroethyl) amine or salt thereof in the preparation of compound of formula Int-B or teneligliptin.

In one embodiment, the present invention provides use of 5-chloro-3-methyl-1-phenyl-1H-pyrazole-4-carbaldehyde or tertiary-butyl-4-(4-formyl-3-methyl-1-phenyl-1H-pyrazol-5-yl) piperazine-1-carboxylate, in the preparation of compound of formula Int-B or teneligliptin.

In one embodiment, the present invention provides a process for the preparation of compound of formula 13 comprising:
a) reacting trans-4-hydroxy-L-proline with amino protecting group to form N-protected-L-trans-4-hydroxyproline;
b) reacting N-protected-L-trans-4-hydroxyproline with 1,3-thiazolidine in presence of hydroxybenzotriazole (HOBt) and 1-(3-Dimethylaminopropyl)-3-ethylcarbodiimide hydrochloride (EDC.HCl) to form N-protected (2S)-4-hydroxy-2-(1,3-thiazolidin-3-ylcarbonyl) pyrrolidine-1-carboxylate;
c) reacting N-protected (2S)-4-hydroxy-2-(1,3-thiazolidin-3-ylcarbonyl)pyrrolidine-1-carboxylate with sulfur trioxide pyridine complex to form N-protected (2S)-4-oxo-2-(1,3-thiazolidin-3-ylcarbonyl)pyrrolidine-1-carboxylate.

In one embodiment, the present invention provides a process for the preparation of compound of formula 15 comprising converting N-benzyl trans-4-hydroxy-2-pyrrolidinylcarbonyl]1,3-thiazolidine to 1-benzyl (2S)-4-oxo-2-(1,3-thiazolidin-3-ylcarbonyl) pyrrolidine, compound of formula 15.

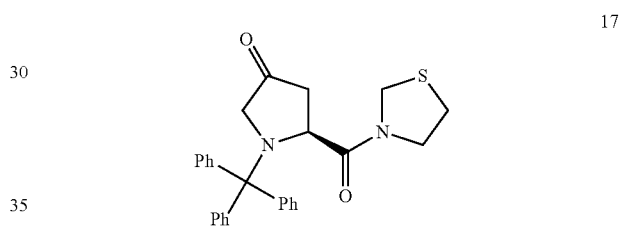

In one embodiment, the present invention provides a process for the preparation of compound of formula 17 comprising converting N-trityl trans-4-hydroxy-2-pyrrolidinylcarbonyl]1,3-thiazolidine to N-trityl -4-oxo-2-pyrrolidinylcarbonyl]1,3-thiazolidine, compound of formula 17.

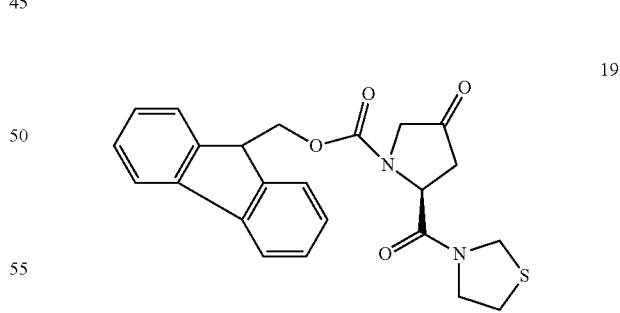

In one embodiment, the present invention provides a process for the preparation of compound of formula 19 comprising converting N-9H-fluoren-9-ylmethyloxycarbonyl-trans-4-hydroxy-2-pyrrolidinylcarbonyl]1,3-thiazolidine to 9H-fluoren-9-ylmethyl (2S)-4-oxo-2-(1,3-thiazolidin-3-ylcarbonyl)pyrrolidine-1-carboxylate, compound of formula 19.

In one embodiment, the present invention provides a process for the preparation of compound of formula 21 comprising converting N-benzyloxycarbonyl-trans-4-hydroxy-2-pyrrolidinylcarbonyl]1,3-thiazolidine to benzyl (2S)-4-oxo-2-(1,3-thiazolidin-3-ylcarbonyl)pyrrolidine-1-carboxylate, compound of formula 21.

21

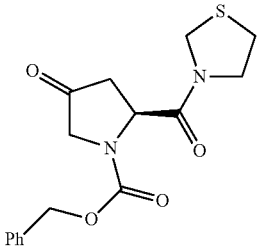

In one embodiment, the present invention provides a process for the preparation of compound of formula 23 comprising converting N-trichloromethyl-trans-4-hydroxy-2-pyrrolidinylcarbonyl]1,3-thiazolidine to trichloromethyl (2S)-4-oxo-2-(1,3-thiazolidin-3-ylcarbonyl)pyrrolidine-1-carboxylate, compound of formula 23.

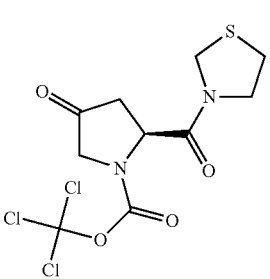

In one embodiment, the present invention provides a process for the preparation of compound of formula 29 comprising converting 1-[(2S, 4R)-4-hydroxy-2-(1,3-thiazolidin-3-ylcarbonyl)pyrrolidin-1-yl]ethanone to (5S)-1-acetyl-5-(1,3-thiazolidin-3-ylcarbonyl)pyrrolidin-3-one to a compound of formula 29.

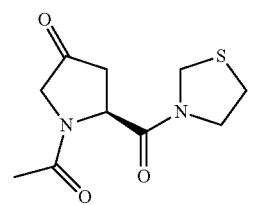

In one embodiment, the present invention provides a process for the preparation of compound of formula 14 as depicted in the below scheme:

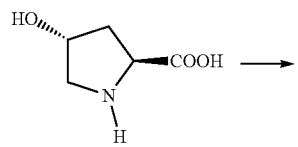

Trans-4-Hydroxy-L-Proline

-continued

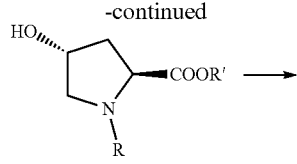

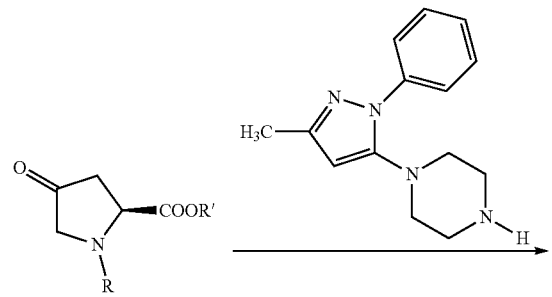

In one embodiment, the present invention provides a process for the preparation of compound of formula 14 comprising:
a) converting trans-4-hydroxy-1-proline to a compound of formula 25 wherein R is same as described above,
b) converting compound of formula 25 to a compound of formula 26,
c) reacting compound of formula 26 with 1-(3-methyl-1-phenyl-1H-pyrazol-5-yl) piperazine or salt thereof to obtain a compound of formula 27; and
d) reacting compound of formula 27 with 1,3-thiazolidine to obtain a compound of formula 14.

While the present invention has been described in terms of its specific embodiments, certain modifications and equivalents will be apparent to those skilled in the art and are intended within the scope of the present invention.

The following examples are provided to enable one skilled in the art to practice the invention and are merely illustrative of the invention. The examples should not be read as limiting the scope of the invention as defined in the claims.

Instrumental Settings for XRPD:

The measurements were performed on Philips X-Ray Diffractometer model XPERT-PRO (PANalytical) Detector: X'celerator [1] using Cu lamp with type and wavelength of the X-ray radiation: K-Alpha1 [A] and 1.54060 under the following conditions: Generator settings: 40 mA/45 kV, Time per step: 50, Step size: 0.0170, Peak width 2.00 and start angle (°) 2.0 and End angle: 50.0, Scan type: continuous; measurement performed at 25° C. The XRPD instrument is calibrated using NIST SRM 6-40C silicon standard and NIST SRM 1976 Alumina.

Sample preparation: About 20 mg of sample was taken and used to fill the groove onto silicon zero background holder using Top-loading technique. The sample holder was then loaded between the X-ray optics-path and scanned using the below described parameters. The obtained powder X-ray diffraction profiles were integrated using High Score Plus Software.

Instrumental Settings for Nuclear Magnetic Resonance (NMR Method) of Teneligliptin 2.5 Hydrbromide Hydrate:

Proton NMR spectra were recorded in $CDCl_3$ and DMSO-$d_6$ using NMR instrument-Varian 300 MHZ. Chemical shifts (δ), in ppm are referred to TMS as internal solvent.

Instrumental Settings for IR:

FTIR spectra were recorded on Spectrum One Perkin-Elmer FTIR spectrophotometer equipped with DTGS detector. The spectra were recorded using KBr disc method in the range from 4000 cm-1 to 450 cm-1 with three scans per sample taking the air as reference. About 200 mg of KBr, previously dried at 200° C. and cooled was weighed, and ground to a fine powder into a mortar. About 2.0 mg of test sample is added and mixed well and ground to a fine powder. A small quantity of powder was used to make a thin semitransparent pellet. This thin pellet is then kept in sample holder which was then loaded to the FTIR Spectrophotometer and scanned between 4000-450 cm-1. The data was processed using Spectrum One Software.

Instrumental settings for HPLC:
Related substances by HPLC:
Reagents and solvents: Water (milli Q equivalent), Methanol (gradient grade), Octane sulphonic acid sodium salt (AR grade), Ortho phosphoric acid (AR grade).
Chromatographic Conditions;
Apparatus: A high performance liquid chromatograph equipped with quaternary gradient pumps, variable wavelength UV detector attached with data recorder and integrator software or equivalent,
Column: Inertsil ODS 3V, 250×4.6 mm, 5μ or equivalent
Mobile phase: A=Buffer, B=Methanol (Gradient Program)
Buffer: 0.01 M Octane sulphonic acid sodium salt in water, pH adjusted to 3.5 with diluted ortho phosphoric acid solution. Filter through 0.45 m filter paper and degas.
Diluent: Buffer: Methanol (10:90 v/v) ; Flow Rate: 1.0 mL/minute
Detection wavelength: UV 210 nm, Column temperature: 25° C., Injection volume: 10 μL;
Run time: 60 minutes
Gradient Program:

| Time (minute) | A % | B % |
|---|---|---|
| 0.01 | 80 | 20 |
| 10 | 40 | 60 |
| 25 | 40 | 60 |
| 35 | 25 | 75 |
| 50 | 25 | 75 |
| 55 | 80 | 20 |
| 60 | 80 | 20 |

It is observed that teneligliptin is eluted at retention time of about 25 minutes and hydrobromide peak (HBr) at retention time of about 1.9 minute.

Preparation of Test Solution: (Prepare in Duplicate)

Weigh accurately about 25 mg of test sample and transfer it into a 25 mL volumetric flask. Add 15 mL of diluent and sonicate to dissolve. Make up to the mark with diluent & mix.

Procedure:

Inject the blank and then inject each of test solution. Record the chromatograms for all injections. Disregard peaks due to blank and hydrobromide. Report the related substances by area normalization method.

EXAMPLES

Example 1

Synthesis of 1,3-thiazolidine

To a saturated solution of sodium carbonate (2.5 kg) in water (17.5 lit), was added cysteamine hydrochloride (500 g, 4.40 mol). The reaction mixture was then cooled at 18-20° C. and added 35-37% formaldehyde solution (350 g) and stirred at 18-20° C. for 2 h. The reaction mixture was extracted with dichloromethane and dried over anhydrous sodium sulphate and concentrated under reduced pressure to yield 375 gram of title compound as an oil. It was used for next step without purification.

$^1$H NMR (300 MHz, $CDCl_3$): δ 2.82-2.887 (t, 2H, J=6.0 Hz), 3.147-3.180 (t, 2H, J=5.8 Hz),) 4.16 (s, 2H) MS (m/z): 90.16 [M+H]$^+$

Example 2

Synthesis of (2S, 4R)-1-[(9H-fluoren-9-ylmethoxy)carbonyl]-4-hydroxypyrrolidine-2-carboxylic acid To a solution of (2S,4R)-4-hydroxy-L-proline (100 g) in tetrahydrofuran (200 ml) was added sodium bicarbonate (80 g), water (400 ml) and 9-fluorenylmethyloxycarbonyl (Fmoc) chloride (226 g) solution (in 200 ml THF) at 25-30° C. The reaction mixture was stirred at about 25-30° C. for about 10-12 h. After completion of reaction, water was added. Then the aq. reaction mass was washed with diisopropyl ether (DIPE) and acidified with 1N hydrochloric acid. The reaction mixture was stirred for about 2-3 hours. The solid was collected by filtration to give the 150 g of title compound as white solid.

$^1$H NMR (300 MHz, DMSO-d6): δ 1.89-2.24 (m, 2H), 3.34-3.43 (m, 2H), 3:43-3.54 (m, 0.5H), 4.12-4.21 (m, 3H), 4.25 (s, 2H), 4.28-4.42 (m, 0.5H), 5.16 (brs, 1H), 7.29-7.34 (m, 2H), 7.38-7.65 (m, 21-1), 7.63-7.65 (m, 2H), 7.87-7.89 (m, 2H)

Melting point:—188-190° C.
Mass-(M+H):—354.33

Example 3

Synthesis of 3-[(2S,4R)-1-fluorenylmethoxycarbonyl-4-hydroxy-2-pyrrolidinylcarbonyl]1,3-thiazolidine.

To a solution of Example-2 compound (100 g) in methylene dichloride (MDC) (500 ml) was added HOBT (hydroxybenzotriazole) (19.11 g), N-methyl morpholine (28.63g) and 1,3 thaizolidine (example—1 compound)

(25.23 g) at 0-5° C. After stirring for 30 min 1-(3-dimethylaminopropyl)-3-ethylcarbodiimide hydrochloride (65.2 g) was added. The above reaction mass was further stirred for 24 hr at 25-30° C. The reaction mixture was monitored by TLC (thin layer chromatography). The reaction mass was then evaporated under reduced pressure. Sodium hydroxide solution (22.64 gm NaOH in 500 ml water) was added to the obtained oily residue. The above aqueous solution was washed with DIPE (diisopropyl ether). Then the pH of aqueous solution was adjusted to 8-9 by 50% HCl aq. solution. The above solution was extracted with ethyl acetate and dried over anhydrous sodium sulphate and concentrated under reduced pressure. The obtained oily compound was crystallised from IPA to yield 55.0 g of title compound as off white solid.

$^1$H NMR (300 MHz, DMSO-d6):—δ 1.85-1.89 (m,1H), 2.17-2.20 (m, 1H), 2.91-3.10 (m, 2H), 3.35-3.63 (m, 5H), 4.17-4.38 (m, 5H), 4.45-4.74 (m,2H), 5.1 (d, 1H), 7.31-7.42 (m, 4H), 7.56-7.65 (m, 2H), 7.87-7.91 (m, 2H).

Mass-(M+H):—425.18.

Example 4

Synthesis of 9H-fluoren-9-ylmethyl-(2S)-4-oxo-2-(1,3-thiazolidin-3-ylcarbonyl) pyrrolidine-1-carboxylate (13 when R=Fmoc)

To a solution of Example-3 compound (25 g) and triethylamine (50 ml) in MDC (50 ml) and dimethyl sulphoxide (250 ml), was added sulphur trioxide pyridine complex (28.15 g) at 0° C. The stirring was continued for about 2 hr at 0-5° C. After completion of reaction, above reaction mass was quenched in aq. HCl solution and extracted with MDC. Then MDC layer was washed with 10% aq. sodium carbonate solution followed by brine and dried over anhydrous sodium sulphate and concentrated under reduced pressure. The obtained brown coloured oily residue was then purified by flash column chromatography (30-40% acetone in hexane) to yield titled compound as cream coloured solid (15.0 gm).

$^1$H NMR (300 MHz, DMSO-d6):—δ 2.43 (m,1H), 2.96-3.12 (m, 2H), 3.60-3.95 (m, 4H), 4.19-4.36 (m,4H), 4.41-4.63 (m, 2H), 4.75-4.83 (m,1H), 5.02-5.11 (m, 1H), 7.31-7.44 (m, 4H), 7.58-7.67 (m, 2H), 7.89-7.91 (m,2H).

Example 5a

Synthesis of 1-(3-methyl-1-phenyl-1H-pyrazol-5-yl) piperazine acetate (Int-B)

Step-1: To a stirred solution of 3-aminocrotononitrile (60 gm,) and 1N HCl (600 ml) was added phenyl hydrazine (72 ml). The reaction mass was strirred for 4 firs at 110-115° C. The reaction mixture was cooled to 25-30° C. and quenched in ice water (3.0 lit). This was then neutralised with sodium bicarbonate solution. The precipitated solid was then stirred, filtered and dried to get 110 gm of the title compound.

$^1$H NMR (300 MHz, DMSO-D$_6$) δ 2.05 (s, 3H), 5.25 (s, 2H), 5.30 (s, 1H), 7.25 (t, 1H, J=6.9 Hz), 7.43 (t, 2H, J=7.8 Hz), 7.56 (d, 2H, J=7.8 Hz); APCI-MS (m/z) 174.25 (M+H)$^+$.

Step-2: To the stirred solution of sodium hydride (60% dispersion in mineral oil, 69 gm, 1.734 mol) and N,N-Dimethyl formamide (DMF400 ml) was slowly added Step-1 compound solution (50 gm, 0.289 mol in 50 ml of DMF) at 0-5° C. and stirred for 0.5 hrs. The bis (2-chloroethyl) amine hydrochloride solution (55 gm) in 50 ml of DMF was added to the reaction mass at 0-5° C. in 30 minutes and stirred for overnight at 25-30° C. The reaction mass was slowly quenched in ice water and then filtered. The aqueous layer was basified with KOH solution and extracted with MDC. The MDC layer was dried over anhydrous sodium sulphate and concentrated under reduced pressure to get crude compound (60 gm). Ethyl acetate, activated carbon was added to the above crude and stirred for 15 minutes at 50° C. The reaction mass was filtered and the bed was washed with ethyl acetate and the filtrate concentrated to get crude compound (60 gm). Toluene and acetic acid was added to the above crude over a period of 15 minutes. The reaction mass was stirred for 2 hrs at 0-5° C. and precipitated solid was filtered and washed with chilled toluene to get 17 gm of acetate salt as white solid.

$^1$H NMR (300 MHz, DMSO-D$_6$) δ 1.87 (s, 3H), 2.14 (s, 3H), 2.72-2.74 (m, 8H), 5.77 (s, 1H), 7.26 (t, 1H, J=7.5 Hz), 7.44 (t, 2H, J=7.8 Hz), 7.74 (d, 2H, J=7.8 Hz).

Example 5b

Synthesis of 1-(3-methyl-1-phenyl-1H-pyrazol-5-yl) piperazine acetate (Int-B)

Step-2: N-Boc bis (2-chloroethyl) amine: To a stirred mixture of bis (2-chloroethyl) amine hydrochloride (20 g) and methylene dichloride (MDC) (100 ml) was added triethyl amine (12.45g) in one lot followed by boc anhydride over a period of 30 minutes at 25-30° C. The resulted reaction mass was stirred for a period of about 12 to about 18 hours at 25-30° C. Water was added to the above reaction mass and the MDC layer separated, dried over anhydrous sodium sulphate and concentrated to get 25 g of light yellow oil.

$^1$H NMR (300 MHz, CDCl$_3$) δ 1.47 (s, 9H), 3.65 (m, 8H). APCI-MS (m/z) 243.43(M+H)$^+$.

Step-3: To the stirred mixture of ex 5a step-1 compound (10 g) and N,N-Dimethylformamide (70 ml) was slowly added sodium hydride (6.9 g), (60% dispersion in mineral oil) at 0-5° C. and stir for 1.0 hr. To this the above step-2 oil (14 g) in 30m1 of DMF) was added at 0-5° C. in 30 minutes and stir for overnight at about 25-30° C. The reaction mass slowly quenched in ice water and filtered via celite bed. The aqueous phase extracted with ethyl acetate. The ethyl acetate phase was dried over anhydrous sodium sulphate and concentrated under reduced pressure to get crude (25 gram). The crude purified by eluting with n-hexane and ethyl acetate (80:20) to get 6 g of product as off white solid.

$^1$H NMR (300 MHz, CDCl$_3$) δ 1.44 (s, 9H), 2.27 (s, 3H), 2.80 (brs, 4H), 3.42 (brs, 4H), 5.67 (s, 1H), 7.26 (t, 1H, J=7.5 Hz), 7.40 (t, 2H, J=7.8 Hz), 7.74 (d, 2H, J=7.8 Hz).

INT-B:

To the stirred solution of step 3 compound (6 g) and methylene dichloride (60 ml) trifluoroacetic acid (30 ml) was added at 25-30° C. and stirred for 1.5 hr. The solvent was evaporated under reduced pressure and water (3.0 lit) was added to this residue. The mixture was washed with diethyl ether. The aqueous layer was basified with sodium bicarbonate solution and the mixture was extracted with chloroform. The chloroform layer dried over sodium sulphate and evaporated under reduced pressure to give residue (4.0 g). Toluene and acetic acid (1 ml) was added over a period of 15 minutes and stirred for 1.5-2.0 hr at 0-5° C. and precipitated solid filtered to get 3.2 g of acetate salt as white solid. $^1$H NMR (300 MHz, DMSO-D$_6$) δ 1.87 (s, 3H), 2.14

(s, 3H), 2.72-2.74 (m, 8H), 5.77 (s, 1H), 7.26 (t, 1H, J=7.5 Hz), 7.44 (t, 2H, J=7.8 Hz), 7.74 (d, 2H, J=7.8 Hz).

Example 6

Synthesis of Teneligliptin Hemipenta Hydrobromide

Step-1: To a solution 9H-fluoren-9-ylmethyl (2,5)-4-oxo-2-(1,3-thiazolidin-3-ylcarbonyl)pyrrolidine-1-carboxylate (12.0 gm), 1-(3-methyl-1-phenyl-1H-pyrazol-5-yl) piperazine acetate (10.3 gm) in dichloromethane (120 ml), was added sodium triacetoxy borohydride (9.02 gm) and the mixture was stirred for 4-5 hrs at 25-30° C. On completion of reaction, water was added to reaction mixture and stirred for 15 min. Organic layer was separated and washed with water and brine solution. The solvent was evaporated under reduced pressure to get the coupled compound (18 gm).

Step-2: To a solution of Step-1 (18.0 g) in dichloromethane (190.0 ml), piperidine (2.90 gm) was added and the reaction mixture was stirred for 5-6 hrs at 25-30° C. After completion, water (60.0 ml) was added to reaction mixture and aq. layer was acidified using hydrochloric acid. The reaction mixture was stirred for 15 min and layers were separated. Aqueous sodium carbonate solution was added to the dichloromethane layer and stirred. Layers were separated and organic layer was given brine wash. Product was isolated by concentrating the organic layer under reduced pressure (10.5 gm).

Methanol (12.0 ml) and tert-Butyl alcohol (96.0 ml) was added to Step-2 product (10.5 gm) and heated to 70-75° C. Aq. HBr (9.0 ml) was slowly added to reaction mixture at 70-75° C. and stirred for 1 hr. Reaction mixture was cooled to 25-30° C. and further stirred for 2-3 hr at 25-30° C. Precipitate was collected by filtration and washed with tert-butyl alcohol (24.0 ml). Obtained solid was dried under reduced pressure at 50-55° C. to get teneligliptin 2.5 hydrobromide crude compound (11.0 gm). Then the product was crystallized by using methanol or mixture of methanol and tert-butyl alcohol to give pure product.

Crystallisation: Crude teneligliptin 2.5 hydrobromide compound (11.0 gm) was dissolved in methanol (22.0 ml) by heating to reflux temperature. The solution was filtered hot. The reaction mixture was allowed to cool and stirred at 25° C. for 1 hr and then at 15-20° C. for 1 hr. The precipitate was collected by filtration, washed with methanol and dried under reduced pressure at 55-60° C. to give pure teneligliptin 2.5 hydrobromide (8.0 gm). Purity by HPLC: 99.7%, chiral purity: 100%, water content: 5.3%, HBr content: 33.8%

XRD table for teneligliptin 2.5 hydrobromide:

| Pos [°2 theta] | Relative Intensity [%] | Pos [°2 theta] | Relative Intensity [%] | Pos [°2 theta] | Relative Intensity [%] |
| --- | --- | --- | --- | --- | --- |
| 10.92 | 6.09 | 21.40 | 36.59 | 28.15 | 66.83 |
| 13.58 | 18.70 | 21.67 | 61.48 | 28.61 | 20.38 |
| 14.61 | 53.32 | 22.17 | 23.49 | 29.10 | 38.11 |
| 16.2 | 10.05 | 22.64 | 46.36 | 30.56 | 11.65 |
| 16.99 | 33.78 | 22.88 | 48.70 | 31.25 | 13.59 |
| 17.19 | 41.26 | 23.21 | 26.12 | 32.09 | 21.70 |
| 17.82 | 33.62 | 23.58 | 38.21 | 32.93 | 16 |
| 18.19 | 26.59 | 24.91 | 56.75 | 34.49 | 12.86 |
| 19.52 | 50.87 | 25.38 | 61.40 | 35.15 | 15.26 |
| 20.18 | 52.19 | 26.67 | 70.07 | 37.50 | 10.96 |
| 20.72 | 17.28 | 27.03 | 100 | 41.81 | 7.23 |

Peak results of HPLC chromatogram.
Peak Results

| | RT | Area | % Area | RT Ratio |
| --- | --- | --- | --- | --- |
| 1 | 18.98 | 7292 | 0.03 | 0.76 |
| 2 | 21.43 | 5625 | 0.03 | 0.85 |
| 3 | 23.83 | 29964 | 0.14 | 0.95 |
| 4 | 25.13 | 20888032 | 99.70 | |
| 5 | 37.88 | 20728 | 0.10 | 1.51 |

Example-7

Acetylation of Trans-4-Hydroxy-L-Proline

To stirred suspension of 4-Hydroxy-L-proline (131 g) in distilled water (300 ml), acetic anhydride (110 ml) was added dropwise over 1 h, slowly the temperature of the reaction mass was increased to 50° C. After addition, the reaction mixture was maintained at 40-50° C. for 2 h. After completion of reaction, acetic acid and water are evaporated under vacuum. Product obtained as viscous syrup which was triturated with acetonitrile to give product as white solid (116 g, yield 70%).

$^1$H NMR (300 MHz, DMSO): δ 1.943 (m, 3H), 2.05-2.08 (m, 1H), 3.33-3.37 (m, 2H), 3.57-3.62 (m, 1H), 4.16-4.21 (m, 1H), 4.31-4.50 (m, 1H), 5.14 (brs, 1H) D$_2$O exchangeable, 12.37 (brs, 1H) D$_2$O exchangeable, MS (m/z): 174.54 [M−H]$^+$, SOR: $[\alpha]_D^{25}$ −105° (c=4, water), Melting Point:—127-132° C.)

Example 8

1-[(2S,4R)-4-Hydroxy-2-(1,3-thiazolidin-3-ylcarbonyl)pyrrolidin-1-yl]ethanone To the solution of N-acetyl-4-hydroxy-L-proline (1.5 g) in methylene dichloride (15 ml), added HOBt (0.61 g), N-methyl morpholine (1.04 g) and 1,3, thaizolidine (0.76 g) at 0-5° C. After stirring for 30 min 1-(3-dimethylaminopropyl)-3-ethylcarbodiimide hydrochloride (2.61 g) was added. The above reaction mass was stirred for 24 h at 25-30° C. Reaction mixture was evaporated under vacuum to give residue which was dissolved in sodium hydroxide solution (2.50 gm NaOH in 20 ml water). The above aqueous solution was washed with diisopropyl ether (DIPE) and separated. Resultant aqueous layer was acidified with 50% HCl aq. solution to pH 8-9. This was extracted with ethyl acetate, dried over anhydrous sodium sulphate and concentrated) under reduced pressure to obtain crude product.

Purified by flash column chromatography (on silica, eluting in 35% ethylacetate in hexane) to yield title compound (0.7 g, Yield 33%).

$^1$H NMR (300 MHz, DMSO-d6):—δ 2.07 (s, 3H), 2.19-2.30 (m, 4H), 3.31 (m, 1H), 3.50-3.53 (m, 1H), 3.79-3.84 (m, 2H), 4.18-4.21 (m, 2H), 4.49-4.77 (m, 4H)MS (m/z): 245.38

Example 9

(5S)-1-acetyl-5-(1,3-thiazolidin-3-ylcarbonyl)pyrrolidin-3-one

To the solution of above pure compound (0.6 g), triethylamine (1.71 ml) in MDC (1.2 ml) and dimethylsulphoxide (3 ml), was added sulphur trioxide pyridine complex (1.5 g, 0.009 mol) at 0° C. It was stirred for further 2 h at 0-5° C. After completion of reaction, above reaction mass was quenched in aq. HCl solution and extracted with MDC. Combined MDC layer was washed with) 10% aq. sodium carbonate solution followed by brine and subsequently dried over anhydrous sodium sulphate and concentrated under reduced pressure. The resultant brown coloured residue was purified by flash column chromatography (35% ethyl acetate in hexane) to yield pure product as viscous oil (200 mg, Yield 35%).

$^1$H NMR (300 MHz, CDCl$_3$): δ 1.98 (s, 3H), 2.91-3.00 (m, 2H), 3.09-3.12 (m, 2H), 3.59-3.63 (m, 2H), 3.92-3.98 (m, 1H), 4.10-4.16 (m, 2H), 4.431-4.35(m, 1H), 4.40-4.50 (m, 1H), 4.62-4.65(m, 1H), 4.91-4.94(m, 1H), 5.10-5.18(m, 1H)MS (m/z): 243.69 [M+H]$^+$

Example 10

Synthesis of
5-Chloro-3-methyl-1-phenyl-1H-pyrazole-4-carbaldehyde

To stir solution of 210 g phosphorous oxychloride (125 ml) added N,N-dimethyl formamide 47.5 g (50 ml) dropwise at 10-15° C. and maintained the reaction mass at 40 min at 25-30° C. 3-methyl-1-phenyl-pyrazole-5-one (25 g) was added to above solution at 25-30° C. The reaction mixture was heated in oil bath at 110-115° c for 1 h. After completion of reaction, it was cooled to 10-15° C. Reaction mixture was quenched in 1500 ml ice water and stirred for 2-3 h at 25-30° C. Product was precipitated and filtered. It was washed with 250 ml water. The obtained wet solid was dried at 60° C. for 12 h to get of 5-chloro-3-methyl-1-phenyl-1H-pyrazole-4-carbaldehyde as light yellow solid (22 g, 70%).

$^1$H NMR (300 MHz, CDCl$_3$): δ 2.4 (s, 3H), 7.54-7.61 (m, 5H), 9.90 (s, 1H),

Melting Point: 133-134° C.

Example 11

Preparation of tert-butyl 4-(4-formyl-3-methyl-1-phenyl-1H-pyrazol-5-yl)piperazine-1-carboxylate A solution of piperazine-1-carboxylic acid tert-butyl ester (2.4 g) in DMF (10 ml) was reacted with 5-chloro-3-methyl-1-phenyl-1H-pyrazole-4-carbaldehyde (1 g) in presence of potassium carbonate (2.17 g) at 25-30° C. The reaction mixture was heated at 120-130° C. for 15 h. It was quenched in water and acidified with conc. HCl at 25° C. then reaction mass was extracted with ethyl acetate three times. Combined ethyl acetate layer was evaporated under vacuum to give 1.9 g as residue which was taken for next step. Pure compound was obtained by column chromatography.

$^1$H NMR (300 MHz, CDCl$_3$): δ 9.94 (s, H), 7.29-7.46 (m, 5H), 3.4(bs, 4H), 3.07 (bs, 4H), 2.4 (s, 3H), 1.4 (s, 9H).MS m/z: 371.6.1 (M+H)+

Example 12

Preparation of
1-(3-methyl-1-phenyl-1H-pyrazol-5-yl)pierazine

A solution of tert-butyl 4-(4-formyl-3-methyl-1-phenyl-1H-pyrazol-5-yl) piperazine-1-carboxylate (1.9 g crude) in methanol (19 ml) was treated with PTSA (p-toluene sulfonic acid 2.9 g) at 80° C. for 2-3 h. After completion of reaction mixture methanol was evaporated and quenched in water and washed with ethyl acetate two times. Aqueous layer basified using sodium carbonate and extracted with MDC. Combined MDC layer was evaporated to give product as solid (0.4 g).

$^1$H NMR (300 MHz, CDCl$_3$): 7.77-7.74 (d, 2H), 7.4-7.38 (t, 2H), 7.26-7.22(t, H), 5.6 (s, H), 2.94-2.86 (m, 8H), 2.27 (s, 3H); MS m/z: 243.77 (M+H)+

Example 13

1-1(2S,4S)-4-[4-(3-methyl-1-phenyl-1H-pyrazol-5-yl)piperazin-1-yl]-2-(1,3-thiazolidin-3-ylcarbonyl) pyrrolidin-1-yl]ethanone Method-A:

To the stirred solution of (5S)-1-acetyl-5-(1,3-thiazolidin-3-ylcarbonyl) pyrrolidin-3-one (5.5 g) and 1-(3-methyl-1-phenyl-1H-pyrazol-5-yl) piperazine (5.8 g) in dichloromethane (55 ml) was added acetic acid (1.15 ml) followed by sodium triacetoxyborohydride (7.3 g). The reaction mixture was stirred for 3-4 h at room temperature. After completion of reaction, water was added and stirred for 15 minutes. The aqueous layer was further extracted by dichloromethane. Combined organic layer was washed with water followed by brine and concentrated under reduced pressure to get 8.6 g of residue as brown oil. It was purified by silica gel column chromatography (5% methanol in ethyl acetate) to give the titled compound (6.6 g).

$^1$H NMR (300 MHz, DMSO-D$_6$): δ 1.48-1.52 (m, 1H), 1.94 (s, 3H), 2.14 (s, 3H), 2.5-2.78 (m, 8H), 2.88-3.2 (m,3H), 3.6-4.79 (m, 8H), 5.79 (s, 1H), 7.27 (t, 1H, J=7.8 Hz), 7.45 (t, 2H, J=7.8 Hz), 7.77 (d, 2H, J=7.8 Hz); ESI-MS (in/z): 469.18 [M+H]$^+$.

Method-B

To the stirred solution of (5S)-1-acetyl-5-(1,3-thiazolidin-3-ylcarbonyl) pyrrolidin-3-one (10 g) and 1-(3-methyl-1-phenyl-1H-pyrazol-5-yl) piperazine (10 g) in dichloromethane (100 ml) was added acetic acid (2.1 ml) followed by sodium triacetoxyborohydride (13.2 g). The reaction mixture was stirred for 3-4 h at 25-30° C. After completion of reaction, water was added and stirred for 15 minutes. The aqueous layer was further extracted by dichloromethane. Combined organic layer was washed with water followed by brine and then concentrated under reduced pressure to give product (18 g).

Example 14

{(2S,4S)-4-[4-(3-methyl-1-phenyl-1H-pyrazol-5-yl) piperazin-1-yl]pyrrolidin-2-yl}(1,3-thiazolidin-3-yl) methanone (teneligliptin)

Method A

To the stirred solution of 3-((2S, 4S)-1-(acetyl)-4-[4-(3-methyl-1-phenyl-1H-pyrazol-5-yl) piperazin-1-yl]pyrrolidin-2-ylcarbonyl) thiazolidine (1.0 gm) in IPA (15.0 ml) was added aqueous hydrobromic acid (2.2 ml, 48% in water) slowly at 80-85° C. The resulting mixture was stirred for 16 h at 80-85° C. After completion of reaction, the reaction mixture was evaporated completely under reduced pressure below 50° C. To the obtained crude oily mass, water (10.0 ml) and ethyl acetate (10.0 ml) were added and stirred. The layers were separated and solid sodium bicarbonate was added to the aqueous layer to attain pH 8. Then aqueous layer was extracted by methylene dichloride, dried over sodium sulphate and evaporated under reduced pressure to get crude oily residue. The residue was purified by silica gel column chromatography (25% methanol in ethyl acetate) to give the titled compound as a solid (360 mg).

$^1$H NMR (300 MHz, DMSO-D$_6$): δ 1.55 (m, 1H), 2.14 (s, 3H), 2.2-2.22(m, 1H), 2.43-2.76(m, 91$^2$), 2.92-3.07 (m, 3H), 3.63-3.84 (m, 4H), 4.42-4.66 (m, 2H), 5.78 (s, 1H)7.24-7.29 (t, 11-1, J=7.5 Hz), 7.43-7.47 (t, 2H, J=7.8 Hz), 7.72-7.75 (d, 2H, 8.1Hz); ESI-MS (m/z): 427.34 [M+H]$^+$.

{(2S,4S)-4-[4-(3-methyl-1-phenyl-1H-pyrazol-5-yl) piperazin-1-yl]pyrrolidin-2-yl}(1,3-thiazolidin-3-yl) methanone 2.5 hydrobromide hydrate.

The above obtained teneligliptin (100.0 mg) was dissolved in ethanol (1.0 ml) at 80° C. and aq. hydrobromic acid (105 mg, 48%) was added at 80° C. The mixture was stirred for 30 min and cooled the mixture gradually at 25-30° C. The precipitated solid was collected by filtration to give title compound (80 mg) as a cream colored solid.

$^1$H NMR (300 MHz, DMSO-D$_6$): δ 2.17 (s, 311), 3.06-3.14 (m, 6H), 3.44 (brs, 4H), 3.7-3.77(m, 21-1), 3.86-4.09 (m, 8H), 4.44-4.75 (m, 3H), 5.95 (s, 1H), 7.32 (t, 11-1, J=7.8Hz), 7.48 (t, 2H, J=7.8 Hz), 7.79 (d, 2H, 7.8 Hz), 9.19 (brs, 1H), 9.93 (brs, 1H).

Method-B:

To the stirred solution of 3-((2S, 4S)-1-(acetyl)-4-[4-(3-methyl-1-phenyl-1H-pyrazol-5-yl) piperazin-1-yl]pyrrolidin-2-ylcarbonyl) thiazolidine (1.0 gm) in IPA (10 ml) was added aqueous hydrobromic acid (2.5 ml, 48% in water) slowly at 80-85° C. The resulting mixture was stirred for 4 h at 80-85° C. After completion of reaction, the reaction mixture was cooled to 25-30° C. and water (30 ml) was added and stirred for 15 min and ethyl acetate (15 ml) was added and stirred. The layers were separated. Aq. layer was basified with 10% sodium carbonate solution (8-9 pH). It was extracted with methylene dichloride. Combined methylene dichloride layer was washed with water 15 ml and dried over sodium sulphate and evaporated under reduced pressure to give title product (0.5 g). It was taken without purification for hydrobromide salt formation. It was dissolved in IPA and filtered. Filtrate was treated with aq hydrobromic acid (0.5 ml) at 25-30° C. for 12 h to give the hydrobromide salt (0.3 g).

Example 15

Crystallisation of Teneligliptin 2.5 Hydrobromide Hydrate Using Methanol and Tert-Butanol Mixture Teneligliptin 2.5 hydrobromide hydrate (23 g) was dissolved in tert-butanol (92 ml) and methanol (235 ml) at reflux temperature. The solution was cooled to 25-30° C. and stirred for 3-4 hours. The solid was filtered and washed with methanol and dried under reduced pressure at 50° C. for 12 h to give teneligliptin 2.5 hydrobromide hydrate (19 g). HPLC 99.43%.

Example 16

Crystallisation of Teneligliptin 2.5 Hydrobromide Hydrate Using n-Butanol and Methanol Mixture Teneligliptin 2.5 hydrobromide hydrate (27 g) was dissolved in n-butanol (108 ml) and methanol (220 ml) at reflux temperature. The solution was cooleds to 25-30° C. and stirred for 3-4 hours. Solid was filtered and washed with methanol and dried under reduced pressure at 50° C. for 12 h to give teneligliptin 2.5 hydrobromide hydrate (20.5 g). HPLC purity 99.6%).

Example 17

Crystallisation of Teneligliptin 2.5 Hydrobromide Hydrate Using DMA and THF Mixture Teneligliptin 2.5 hydrobromide hydrate (10.0 g) was dissolved in DMA (dimethyl acetamide 100 ml). To this solution THF (tetrahydrofuran, 350 ml) was added at 25-30° C. The solution was stirred for 3-4 hours: Solid was filtered and washed with THF and dried under reduced pressure at 50° C. for 12 h to give teneligliptin 2.5 hydrobromide hydrate (9.0 g). HPLC purity 99.25%.

Example 18

Crystallisation of Teneligliptin 2.5 Hydrobromide Hydrate Using DMF and THF Mixture Teneligliptin 2.5 hydrobromide hydrate (10.0 g) was dissolved in DMF (dimethyl formamide 100 ml). To this solution THF (tetrahydrofuran 250 ml) was added at 25-30° C. The solution was cooled to 25-30° C. and stirred for about 12-20 hours for. Solid was filtered and washed with THF and dried under reduced pressure at 50° C. for 12 h to give teneligliptin 2.5 hydrobromide hydrate (8.25 g). HPLC purity 99.3%.

The invention claimed is:

1. A process for the preparation of teneligliptin, a compound of formula I or salt or hydrate thereof, the process comprising:

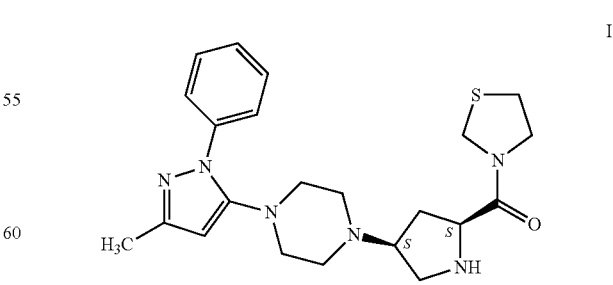

I (a)(i) reacting a compound of formula 11, with bis (2-chloroethyl) amine or N-protected derivative or salt thereof to obtain a compound of formula Int-B or an N-protected derivative or salt thereof,

11

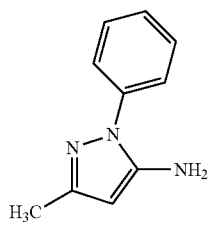

Or (a)(ii) reacting 5-chloro-3-methyl-1-phenyl-1H-pyrazole-4-carbaldehyde, a compound of formula 30 with piperazine or N-protected derivative thereof,

30

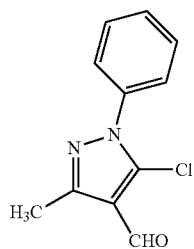

to obtain a compound of formula Int-B or an N-protected derivative or salt thereof;

Int-B

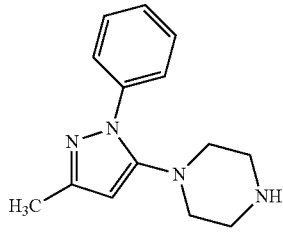

(b) reacting the compound of formula Int-B or N-protected derivative or salt thereof with a compound of formula 13 to obtain a compound of formula 14,

13

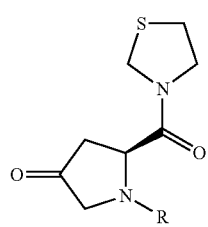

14

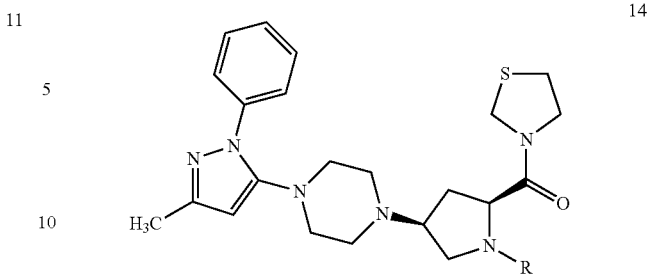

wherein R is an amino protecting group selected from the group consisting of aralkyl, acyl, lower alkoxycarbonyl, aralkyloxycarbonyl, lower alkanesulfonyl, aryl sulfonyl, tri-(loweralkyl) silyl, and triphosgene; and (c) deprotecting the compound of formula 14 to obtain teneligliptin, a compound of formula I or salt or hydrate thereof.

2. The process according to claim 1, wherein in step (a)(ii) 5-chloro-3-methyl-1-phenyl-1H-pyrazole-4-carbaldehyde, the compound of formula 30

30

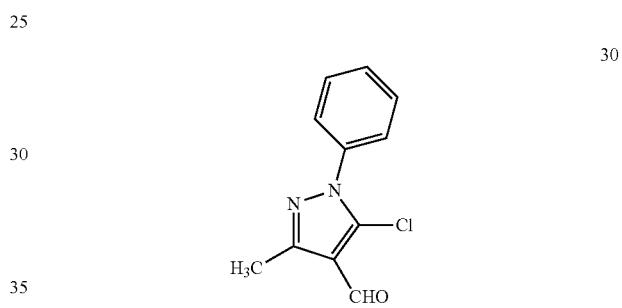

31

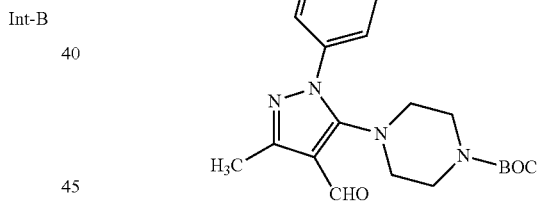

is reacted with piperazine-1-carboxylic acid tert-butyl ester to obtain tert-butyl 4-(4-formyl-3-methyl-1-phenyl-1H-pyrazol-5-yl)piperazine-1-carboxylate, a compound of formula 31 which is further deprotected to obtain the compound of formula Int-B.

3. The process according to claim 1, wherein in step (b) R is acetyl, and the process further comprises reacting a compound of formula 29 with a compound of formula Int-B to obtain a compound of formula 32

29

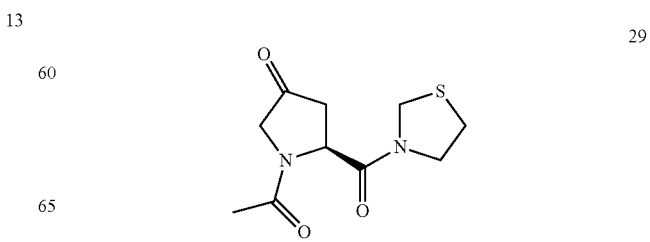

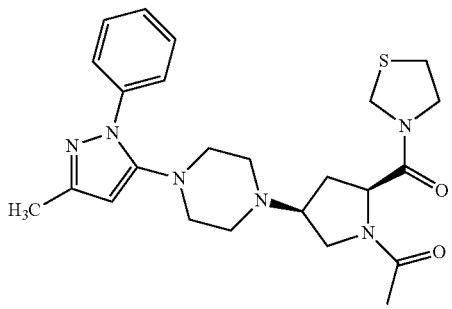

32

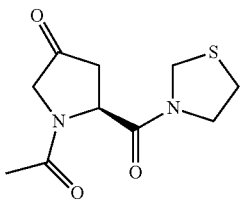

29 or reacting a compound of formula 19 with a compound of formula Int-B to obtain a compound of formula 20

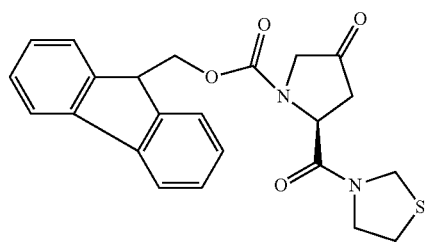

19 20

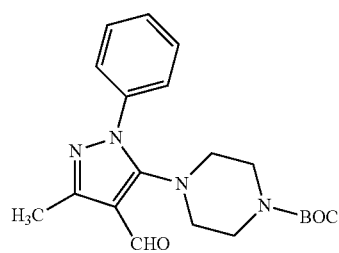

31

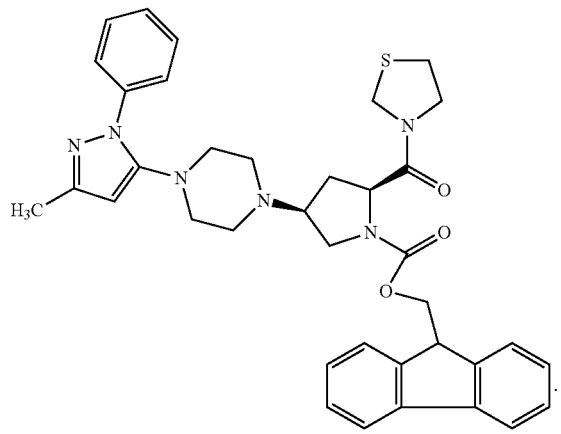

20

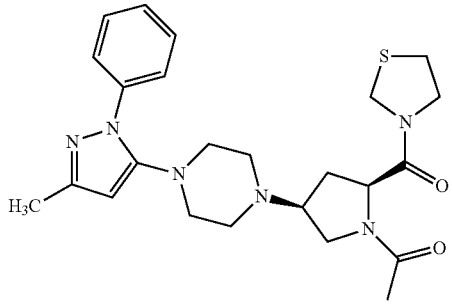

32 as measured by high performance liquid chromatography.

8. The process according to claim 1 wherein the step of deprotecting is carried out with a reagent selected from the group consisting of acid, reducing agents and base.

9. The process according to claim 1, wherein step b involves either reacting Int-B with the compound of formula 19 which is selected from the compound of formula 13 when R is 9-fluorenylmethyloxycarbonyl to obtain the compound of formula 20; or reacting Int-B with the compound of formula 29 which is selected from the compound of formula 13 when R is acetyl to obtain the compound of formula 32

4. The process according to claim 1, wherein the teneligliptin is treated with hydrobromic acid to obtain teneligliptin 2.5 hydrobromide hydrate.

5. The process according to claim 4, comprising crystallizing teneligliptin 2.5 hydrobromide or a hydrate thereof from a solvent selected from the group consisting of methanol, n-butanol, tertiary butanol, dimethyl acetamide, dimethyl formamide, tetrahydrofuran, propyl acetate, isopropyl acetate, methyl ethyl ketone, methyl isobutyl ketone and mixtures thereof.

6. The process according to claim 5, wherein teneligliptin 2.5 hydrobromide hydrate is crystallised from methanol.

7. The process according to claim 5, wherein the obtained teneligliptin 2.5 hydrobromide hydrate is substantially pure teneligliptin 2.5 hydrobromide hydrate having a purity of at least 99% and having less than 0.1% of any of the below compounds

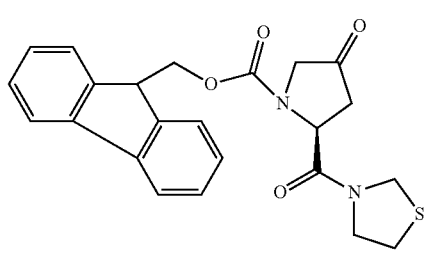

19

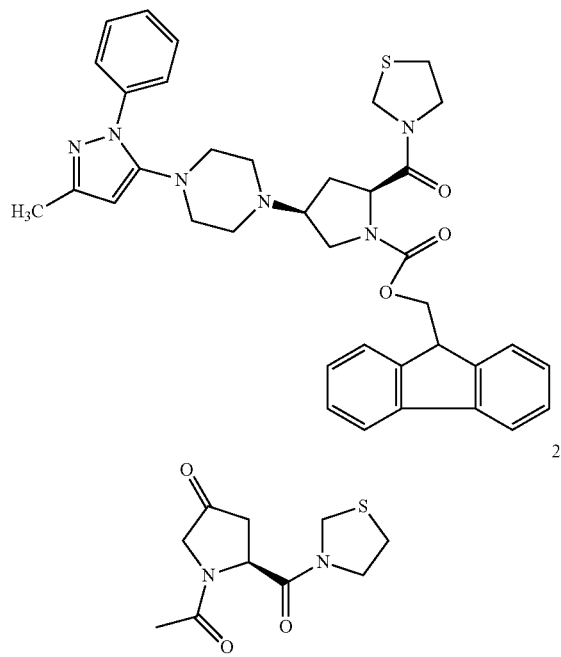
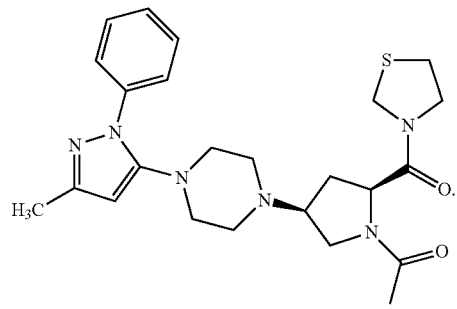
10. The process according to claim 1, comprising step (a)(ii) wherein 5 chloro-3-methyl-1-phenyl-1H-pyrazole-4-carbaldehyde is reacted with piperazine or N-protected derivative thereof to obtain the compound of formula Int-B or an N-protected derivative or salt thereof.
* * * * *